(12) United States Patent
Carbone et al.

(10) Patent No.: US 6,974,460 B2
(45) Date of Patent: Dec. 13, 2005

(54) BIASED ANGULATION BONE FIXATION ASSEMBLY

(75) Inventors: John Carbone, Lutherville, MD (US); Aaron Markworth, Pompton Lakes, NJ (US); Michael Horan, Charleston, SC (US); Yves Crozet, Ramsey, NJ (US)

(73) Assignee: Stryker Spine (FR)

( * ) Notice: Subject to any disclaimer, the term of this patent is extended or adjusted under 35 U.S.C. 154(b) by 256 days.

(21) Appl. No.: 10/091,068

(22) Filed: Mar. 5, 2002

(65) Prior Publication Data

US 2003/0055426 A1 Mar. 20, 2003

Related U.S. Application Data

(60) Provisional application No. 60/322,042, filed on Sep. 14, 2001.

(51) Int. Cl.[7] .............................................. A61B 17/70
(52) U.S. Cl. ............................................ 606/61; 606/60
(58) Field of Search ........................ 606/61, 69, 60, 606/70, 71, 72, 73, 78, 53

(56) References Cited

U.S. PATENT DOCUMENTS

| | | | |
|---|---|---|---|
| 4,484,570 A | 11/1984 | Sutter et al. | |
| 4,805,602 A | 2/1989 | Puno et al. | |
| 4,946,458 A | 8/1990 | Harms et al. | |
| 5,084,048 A | * 1/1992 | Jacob et al. | 606/61 |
| 5,129,388 A | 7/1992 | Vignaud et al. | |
| 5,133,717 A | * 7/1992 | Chopin | 606/61 |
| 5,176,678 A | 1/1993 | Tsou | |
| 5,190,543 A | 3/1993 | Schläpfer | |
| 5,207,678 A | 5/1993 | Harms et al. | |
| 5,217,497 A | 6/1993 | Mehdian | |
| 5,246,442 A | 9/1993 | Ashman et al. | |
| 5,253,406 A | 10/1993 | Shere et al. | |
| 5,344,422 A | 9/1994 | Frigg | |
| 5,360,431 A | 11/1994 | Puno et al. | |
| 5,403,314 A | 4/1995 | Currier | |
| 5,439,381 A | 8/1995 | Cohen | |
| 5,443,467 A | 8/1995 | Biedermann et al. | |
| 5,466,237 A | 11/1995 | Byrd, III et al. | |
| 5,474,551 A | * 12/1995 | Finn et al. | 606/61 |
| 5,474,555 A | 12/1995 | Puno et al. | |
| 5,476,464 A | 12/1995 | Metz-Stavenhagen et al. | |
| 5,496,321 A | 3/1996 | Puno et al. | |
| 5,531,746 A | 7/1996 | Errico et al. | |
| 5,549,608 A | 8/1996 | Errico et al. | |
| 5,554,157 A | 9/1996 | Errico et al. | |
| 5,584,831 A | 12/1996 | McKay | |

(Continued)

FOREIGN PATENT DOCUMENTS

| | | |
|---|---|---|
| CA | 2216955 | 10/1996 |
| DE | 195 42 116 A1 | 5/1997 |
| EP | 0 885 598 A2 | 12/1996 |
| WO | WO 88/03781 | 6/1988 |
| WO | WO 98/34554 | 8/1998 |
| WO | WO 01/47425 A1 | 5/2001 |

Primary Examiner—Jessica R. Baxter
(74) Attorney, Agent, or Firm—Lerner, David, Littenberg, Krumholz & Mentlik, LLP

(57) ABSTRACT

A bone fixation assembly including a coupling element having an inner surface defining a first bore coaxial with a first longitudinal axis, and a second bore coaxial with a second longitudinal axis, whereby the second longitudinal axis intersects the first longitudinal axis. The coupling element has a seat adjacent the lower end of the coupling element, the seat being defined by the inner surface of the coupling element. The assembly includes an anchoring element assembled with the coupling element, the anchoring element having a first end for insertion into bone and a head spaced from the first end, the head being in contact with the seat of the coupling element. The assembly provides sufficient angulation between adjacent anchoring elements securing a common orthopedic rod, and is particularly useful for assemblies mounted in spines having abnormal curvatures and in the cervicothoracic region of the spine.

39 Claims, 23 Drawing Sheets

U.S. PATENT DOCUMENTS

| | | |
|---|---|---|
| 5,586,984 A | 12/1996 | Errico et al. |
| 5,591,166 A | 1/1997 | Bernhardt et al. |
| 5,609,593 A | 3/1997 | Errico et al. |
| 5,647,873 A | 7/1997 | Errico et al. |
| 5,669,911 A | 9/1997 | Errico et al. |
| 5,672,176 A | 9/1997 | Biedermann et al. |
| 5,690,630 A | 11/1997 | Errico et al. |
| 5,725,527 A | 3/1998 | Biedermann et al. |
| 5,725,528 A | 3/1998 | Errico et al. |
| 5,733,285 A | 3/1998 | Errico et al. |
| 5,733,286 A | 3/1998 | Errico et al. |
| 5,735,850 A | 4/1998 | Baumgartner et al. |
| 5,735,852 A | 4/1998 | Amrein et al. |
| 5,752,957 A | 5/1998 | Ralph et al. |
| 5,797,911 A | 8/1998 | Sherman et al. |
| 5,810,818 A | 9/1998 | Errico et al. |
| 5,873,878 A | 2/1999 | Harms et al. |
| 5,879,350 A | 3/1999 | Sherman et al. |
| 5,882,350 A | 3/1999 | Ralph et al. |
| 5,885,286 A | 3/1999 | Sherman et al. |
| 5,891,145 A | 4/1999 | Morrison et al. |
| 5,946,988 A | 9/1999 | Metz-Stavenhagen |
| 5,951,533 A | 9/1999 | Freeman |
| 5,997,539 A | 12/1999 | Errico et al. |
| 6,030,389 A | 2/2000 | Wagner et al. |
| 6,053,917 A | 4/2000 | Sherman et al. |
| 6,063,089 A | 5/2000 | Errico et al. |
| 6,063,090 A | 5/2000 | Schläpfer |
| 6,074,391 A | 6/2000 | Metz-Stavenhagen et al. |
| 6,077,262 A | 6/2000 | Schläpfer et al. |
| 6,090,110 A | 7/2000 | Metz-Stavenhagen |
| 6,090,111 A | 7/2000 | Nichols |
| 6,113,601 A | 9/2000 | Tatar |
| 6,280,442 B1 | 8/2001 | Barker et al. |
| 6,325,802 B1 | 12/2001 | Frigg |
| 6,443,953 B1 | 9/2002 | Perra et al. |
| 6,554,834 B1 * | 4/2003 | Crozet et al. .................. 606/65 |
| 2001/0034522 A1 | 10/2001 | Frigg |

* cited by examiner

FIG. 8
FIG. 9
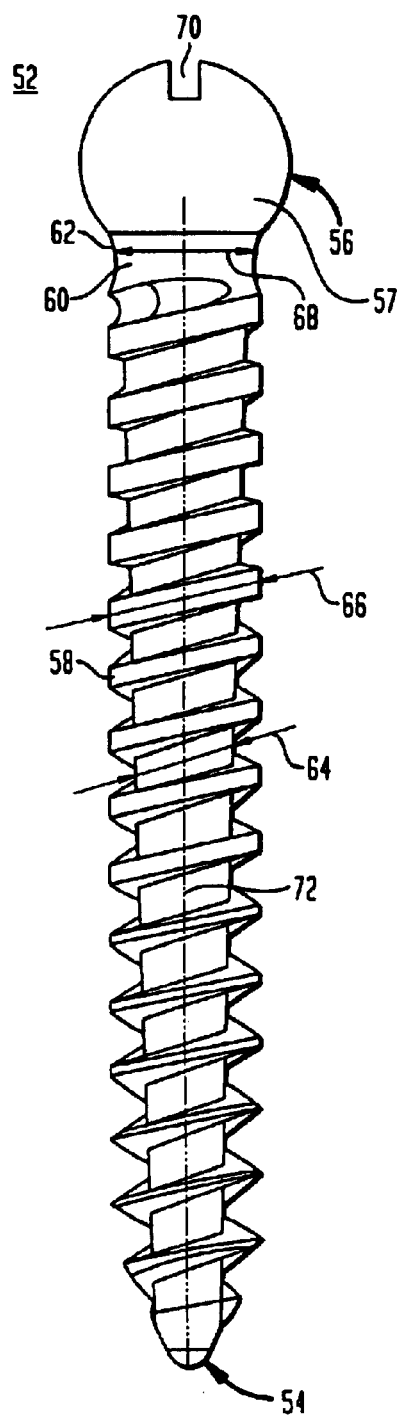
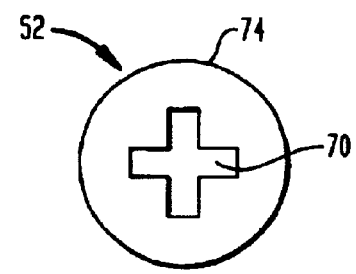

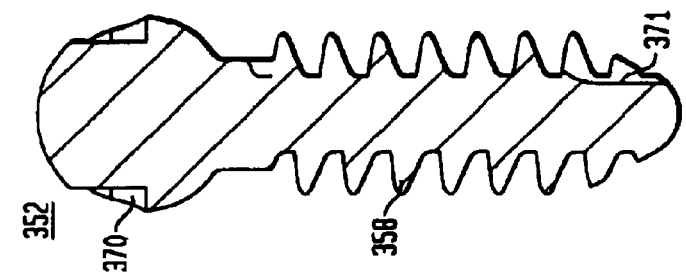
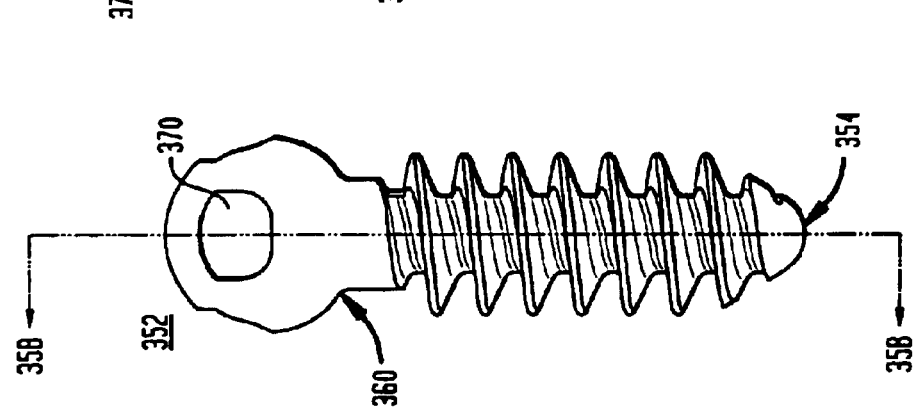
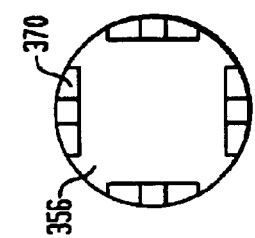
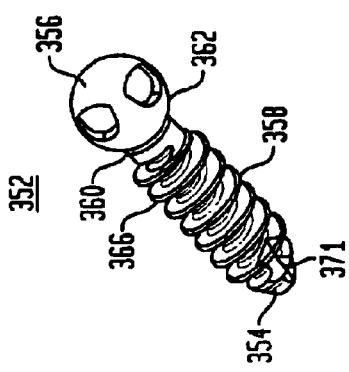

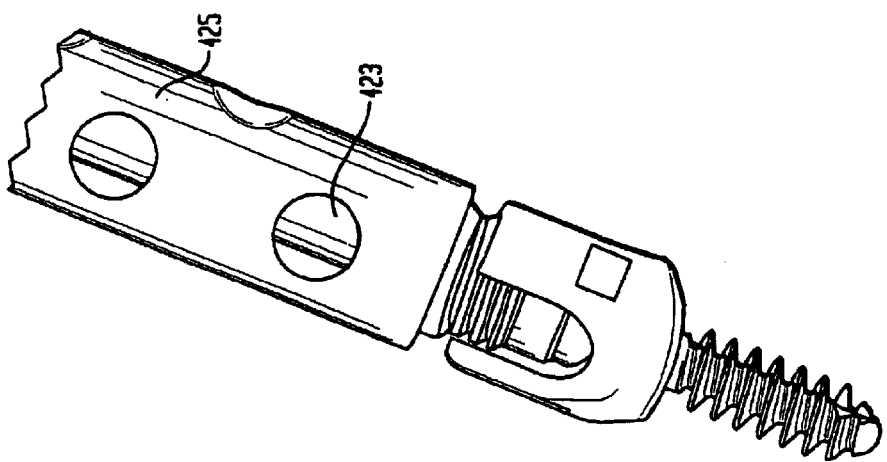
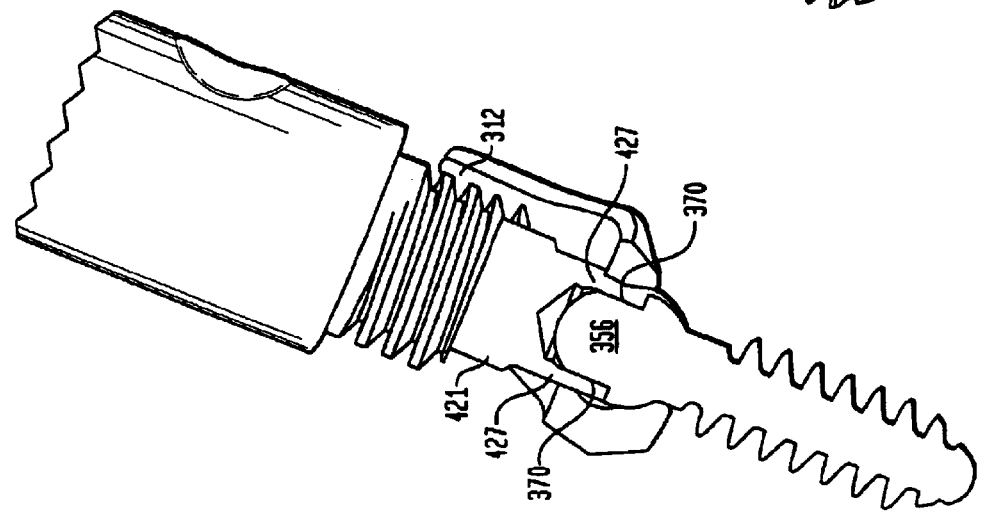
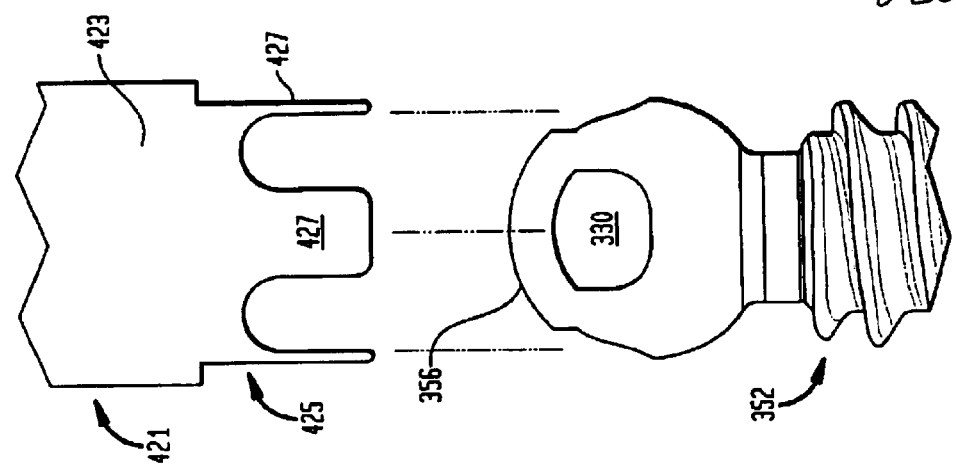

BIASED ANGULATION BONE FIXATION ASSEMBLY

CROSS-REFERENCE TO RELATED APPLICATIONS

The present application claims benefit of U.S. provisional application No. 60/322,042, filed Sep. 14, 2001, the disclosure of which is hereby incorporated by reference herein.

FIELD OF THE INVENTION

The present invention relates generally to spinal fixation devices and more specifically relates to pedicle fixation assemblies.

BACKGROUND OF THE INVENTION

The spinal column is a highly complex system of bones and connective tissues that provides support for the body and protects the delicate spinal cord and nerves. The spinal column includes a series of vertebral bodies stacked one atop the other, each vertebral body including an inner or central portion of relatively weak cancellous bone and an outer portion of relatively strong cortical bone. Situated between each vertebral body is an intervertebral disc that cushions and dampens compressive forces exerted upon the spinal column. A vertebral canal containing the spinal cord and nerves is located behind the vertebral bodies.

There are many types of spinal column disorders including scoliosis (abnormal lateral curvature of the spine), kyphosis (abnormal forward curvature of the spine, usually in the thoracic spine), excess lordosis (abnormal backward curvature of the spine, usually in the lumbar spine), spondylolisthesis (forward displacement of one vertebra over another, usually in a lumbar or cervical spine) and other disorders caused by abnormalities, disease or trauma, such as ruptured or slipped discs, degenerative disc disease, fractured vertebra, and the like. Patients that suffer from such conditions usually experience extreme and debilitating pain, as well as diminished nerve function.

Surgical techniques commonly referred to as spinal fixation uses surgical implants for fusing together and/or mechanically immobilizing two or more vertebral bodies of the spinal column. Spinal fixation may also be used to alter the alignment of adjacent vertebral bodies relative to one another so as to change the overall alignment of the spinal column. Such techniques have been used effectively to treat the above-described conditions and, in most cases, to relieve pain.

There are many disadvantages associated with current spinal fixation devices. FIG. 1 show a prior art bone fixation device that is incapable of capturing spine rods when the rod capturing assemblies must be rotated to extreme angles. The design limits pivotal movement to an angle θ.

One spinal fixation technique involves immobilizing the spine using orthopedic stabilizing rods, commonly referred to as spine rods, which run generally parallel to the spine. This may be accomplished by exposing the spine posteriorly and fastening bone screws to the pedicles of vertebral bodies. The pedicle screws are generally placed two per vertebra and serve as anchor points for the spine rods. Clamping elements adapted for receiving a spine rod therethrough are then used to join the spine rods to the pedicle screws. The aligning influence of the spine rods forces the spinal column to conform to a more desirable shape. In certain instances, the spine rods may be bent to achieve the desired curvature of the spinal column.

U.S. Pat. No. 5,129,388 to Vignaud et al. discloses a spinal fixation device including a pedicle screw having a U-shaped head rigidly connected to an upper end of the screw. The U-shaped head includes two arms forming a U-shaped channel for receiving a spine rod therein. The U-shaped head is internally threaded so that a setscrew having external threads may be screwed therein. After the pedicle screw has been inserted into bone and a spine rod positioned in the U-shaped channel, the set screw is threaded into the internal threads of the U-shaped channel for securing the spine rod in the channel and blocking relative movement between the spine rod and the pedicle screw. The fixation device also includes a cap covering an upper portion of the U-shaped head to prevent the arms from spreading apart as the set screw is threaded into the internal threads of the U-shaped head.

Surgeons have encountered considerable difficulty when attempting to insert spinal fixation devices such as those disclosed in the above-mentioned '388 patent. This is because the U-shaped heads atop adjacent screws are often out of alignment with one another due to curvature of the spinal column and the different orientation of adjacent pedicles receiving the screws. As a result, spine rods must often be bent in multiple planes in order to pass the rods through adjacent U-shaped channels. This "bending the spine rod" solution serves to weaken the strength of the assembly and results in significantly longer operations, which increases the likelihood of surgical complications.

In response to the above-noted problems, U.S. Pat. No. 5,733,286 to Errico et al., U.S. Pat. No. 5,672,176 to Biedermann et al., and U.S. Pat. No. 5,476,464 to Metz-Stavenhagen disclose polyaxial spinal fixation devices wherein the anchoring element fixed to the bone has a spherically-shaped head. The fixation devices in the above-identified patents also have orthopedic rod capturing assemblies for securing orthopedic rods in the capturing assemblies and connecting the rods with the anchoring elements. The spherically shaped heads of the anchoring elements permit movement of the rod capturing assemblies relative to the anchoring elements.

In spite of the above-mentioned devices, there remains a need for improved spinal fixation devices. In particular, there remains a need for spinal fixation devices that provide an increased degree of angulation between the rod capturing assemblies and the anchoring elements so as to facilitate capturing orthopedic stabilizing rods within the rod capturing assemblies.

SUMMARY OF THE INVENTION

In one preferred embodiment of the present invention, a fixation assembly includes a coupling element having a first section with a first bore coaxial with a first longitudinal axis and a second section with a second bore coaxial with a second longitudinal axis transverse to the first longitudinal axis. The first bore extends from an upper end of the coupling element and the second bore extends from the lower end of the coupling element. The coupling element also includes rod-receiving openings extending from the upper end thereof. The fixation assembly anchoring element having a first end for insertion into bone and a longitudinal axis. The first and second bores of the coupling element extend in directions that are tilted with respect to one another, as their associated first and second longitudinal axes are disposed transversely to one another. Due to the biased angulation of the coupling element, the coupling element can be manipulated to cover a broader range of angles for capturing an orthopedic stabilizing rod.

In certain preferred embodiments, the anchoring element is integrally connected to a lower end of the coupling element. In other preferred embodiments, the anchoring element comprises a separate member assembled with the coupling element, whereby the coupling element and anchoring element are pivotable and rotatable relative to one another for capturing a spine rod in the rod receiving openings of the coupling element.

Achieving sufficient angulation between anchoring elements while engaging the orthopedic rod is essential for assemblies mounted in spines having abnormal curvatures. Sufficient angulation is also important in the cervicothoracic junction of the spine.

After being assembled together, the coupling element and the anchoring element are preferably pivotable and rotatable relative to one another. The coupling element preferably includes a seat adjacent the lower end thereof that is shaped to facilitate pivotal movement of the coupling element and anchoring element relative to one another.

In certain preferred embodiments, the seat is shaped to allow the coupling element to pivot with respect to the anchoring element. Before the coupling element is locked into place with respect to the anchoring element, the coupling element is pivotable and rotatable for capturing a spine rod in the rod receiving openings thereof. The combination of the pivotable coupling element and the tilted arrangement of the first and second portions of the coupling element enable the coupling element to move over a broader range of angles for capturing a spine rod.

The anchoring element preferably has a second end remote from the first end, and a head at the second end having an underside for engaging the seat. The assembly preferably includes a locking element engageable with the coupling element for locking the rod in the coupling element, after the rod has been received in the rod-receiving openings. The locking element forces the head against the seat of the coupling element to lock the position of the coupling element with respect to the anchoring element.

The head may have a depression adapted to receive a driver for driving the anchoring element into bone. The depression in the head may be one or more slots or a hexagonal opening. The anchoring element may include a neck between the head and the first end thereof. The neck preferably has a reduced diameter portion for facilitating pivotal movement of the coupling element and the anchoring element relative to one another. The reduced diameter neck may have a concave surface located adjacent an underside of the head.

The head and seat may have many shapes. In certain preferred embodiments, the head has an underside with a convex shape for engaging the seat. The seat may be defined by an interior wall of the coupling element having an inwardly tapering conical shape. In other preferred embodiments, the seat may be defined by an interior wall of the coupling element having a convex or spherical shape.

The coupling element preferably has an exterior surface, an upper end and a lower end, and rod-receiving openings that are open on the upper end and extend toward the lower end. The coupling element preferably has cuts formed between the exterior surface and the rod-receiving openings for minimizing the width of the coupling element. As a result, adjacent coupling elements may be more closely packed adjacent one another, because the cuts result in the coupling elements having less width.

In certain preferred embodiments, the anchoring element is a screw fastener having screw threads extending between the first and second ends thereof. The anchoring element may include barbs on an outer surface thereof so that withdrawal of the anchoring element from bone is hindered by the barbs. The anchoring element may also include an elongated shaft having holes defined therein for receiving bone graft material or allowing ingrowth of bone. The anchoring element may also include a hook for anchoring into bone.

The coupling element may include a chamfer adjacent the first bore for facilitating assemblies of the anchoring element with the coupling element. The coupling element may have opening surfaces defining the rod receiving openings and the chamfer may extend from one of the opening surfaces to an inner surface defining the first bore.

In another preferred embodiment of the present invention, a bone fixation assembly includes a coupling element having an upper end defining a first plane and having rod receiving openings, a lower end defining a second plane that intersects the first plane, and at least one bore extending between the upper and lower ends. The at least one bore is adapted to receive an anchoring element. The assembly includes an anchoring element having a first end insertable into bone that is assembled with the coupling element.

The head of the anchoring element preferably has one or more depressions formed therein adapted for receiving a driver for driving the anchoring element into bone. The anchoring element preferably includes a reduced diameter neck for facilitating pivotal movement of the coupling element with respect to the anchoring element.

In further preferred embodiments of the invention, a coupling element has an upper end and a lower end and comprises a first section extending from the upper end toward the lower end of the coupling element. The first section has a first bore coaxial with a first longitudinal axis. The coupling element has a second section extending from the lower end toward the upper end of the coupling element. The second section has a second bore coaxial with a second longitudinal axis transverse to the first longitudinal axis. As a result, the first and second bores extend in directions that are angled relative to one another. The coupling element includes rod-receiving openings extending from the upper end toward the lower end that are adapted to receive an orthopedic rod.

The inner surface of the coupling element adjacent upper end preferably includes threads for engaging external threads on a locking element for locking an orthopedic rod with the coupling element. The locking element is threaded into the internal threads of the coupling element after spine rod has been captured in rod receiving openings.

In certain preferred embodiments, the coupling element has an outer surface with gripping notches for engagement by an instrument so that the coupling element may be positioned with respect to an orthopedic rod. The notches may include indentations or protrusions provided therein for centering the instrument on the coupling element.

In still another preferred embodiment of the present invention, a coupling element for a pedicle screw assembly comprises an upper end defining a first plane, a lower end defining a second plane, and at least one bore extending between the upper and lower ends adapted to receive an anchoring element. The first and second planes intersect one another. The first plane and the second plane preferably have an intersection defining an angle of about 20–30°. In more preferred embodiments, the angle between the first and second intersecting planes is about 25°±2°. In highly preferred embodiments, the angle between the intersecting planes is approximately 24°.

In yet another preferred embodiment of the present invention, a coupling element for a pedicle screw assembly includes a first section at an upper end of the coupling element, the first section having a first bore coaxial with first longitudinal axis, and a second section at a lower end of the coupling element, the second section having a second bore coaxial with a second longitudinal axis. The first and second longitudinal axes preferably intersect one another. The assembly includes an anchoring element, such as a screw thread. The bone anchoring portion of the anchoring element is adapted to project through the second bore opening at the lower end of the coupling element when the coupling element and anchoring element are assembled together.

In still another preferred embodiment of the present invention, a method of stabilizing an area of the spine includes anchoring an anchoring element into bone. The anchoring element is assembled with a coupling element having a first bore and a second bore that are tilted with respect to one another. The anchoring element projects through the second bore opening at a lower end of the coupling element so that the coupling element and anchoring element are movable relative to one another. The position of the coupling element is adjustable with respect to the anchoring element so that rod receiving openings extending from an upper end of the coupling element may receive an orthopedic rod. After the rod is captured in the rod-receiving openings, the position of the coupling element is locked with respect to the anchoring element using a locking element that exerts a downward locking force on the spine rod, which in turn forces the head of the anchoring element into the seat of the coupling element.

The coupling element desirably has the first bore extending through the first section and the second bore extending through the second section. The anchoring element and coupling element are preferably assembled by inserting the anchoring element into the first bore.

Before the coupling element and anchoring element are locked, the position of the coupling element may be adjusted by pivoting the coupling element with respect to the anchoring element so that the rod receiving openings engage an orthopedic rod disposed at a position displaced from the longitudinal axis of the anchoring element.

BRIEF DESCRIPTION OF THE DRAWINGS

These and other objects, features and advantages of the present invention will be more readily apparent from the detailed description of preferred embodiments set forth below, taken in conjunction with the accompanying drawings, in which:

FIG. 8 is a front elevation view of an anchoring element, in accordance with certain preferred embodiments of the present invention.

FIG. 9 is a top plan view of the anchoring element of FIG. 8.

FIG. 32B-1 shows an expanded view of a section of the coupling element shown in FIG. 32B.

FIG. 33 shows a perspective view of an anchoring element of a bone fixation assembly, in accordance with certain preferred embodiments of the present invention.

FIG. 34 shows a top plan view of the anchoring element shown in FIG. 33.

FIGS. 35A and 35B show respective side elevation and cross-sectional views of the anchoring element shown in FIG. 33.

FIG. 40 shows a fragmentary view of a driver including a lower end having spaced fingers for engaging a head of an anchoring element, in accordance with certain preferred embodiments of the present invention.

FIG. 41 shows a cross-sectional view of the driver of FIG. 41 engaging the head of the anchoring element.

FIG. 42 shows a perspective view of the driver of FIG. 42 engaging the head of the anchoring element.

DETAILED DESCRIPTION OF PREFERRED EMBODIMENTS

Figure 1:
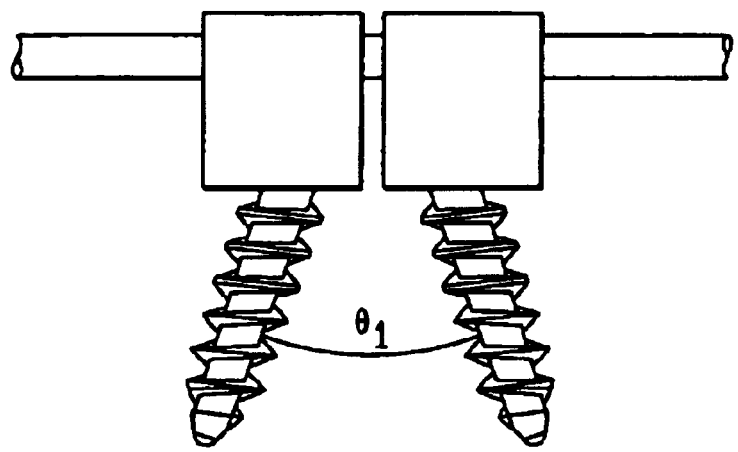
FIG. 1 shows a side elevation view of a prior art bone fixation assembly.
Figure 2:
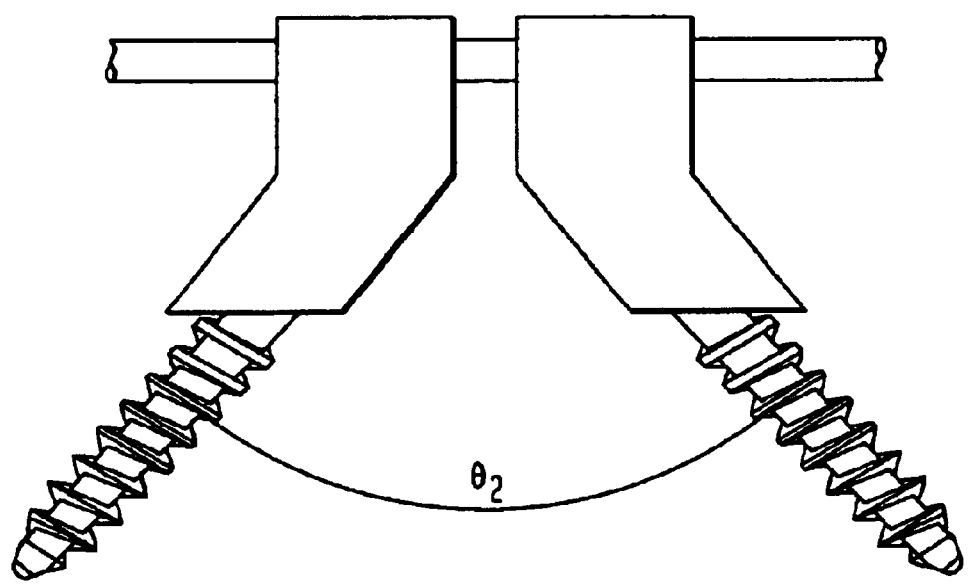
FIG. 2 shows a simplified view of a pair of bone fixation assemblies coupled with an orthopedic stabilizing rod, in accordance with certain preferred embodiments of the present invention.
Figure 3:
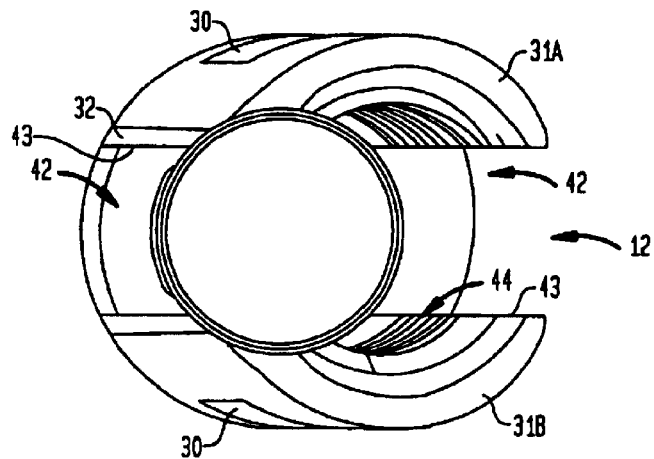
FIG. 3 is a top plan view of a coupling element of a bone fixation assembly, in accordance with a preferred embodiment of the present invention.

Referring to FIG. 2, the present invention is generally related to providing bi-axial coupling elements that are capable of pivoting over a broader range of angles (e.g. to an angle $\theta_2$ of up to about 110°), thereby providing for greater angulation than is possible with the prior art devices shown in FIG. 1.

FIGS. 3–16 show a bone fixation assembly, in accordance with certain preferred embodiments of the present invention. The bone fixation assembly may be secured to the pedicles of vertebral bodies of a spinal column. Referring to FIGS. 3–7, the fixation assembly includes a coupling element 12 preferably made of a biologically inert material, preferably any metal customarily used for surgical devices and particularly those used for bone screws and pins, such as titanium or stainless steel. Other suitable materials for the coupling element include alloys, composite materials, ceramics or carbon fiber materials. Coupling element 12 has an upper end 14 and a lower end 16. The upper end 14 defines a first plane 23 and the lower end 16 defines a second plane 25, the first and second planes 23, 25 preferably intersecting one another.

The coupling element 12 includes a first section 18 that extends from upper end 14 to an intermediate region 20, and a second section 21 that extends from intermediate region 20 to lower end 16. The first section 18 has a first bore extending therethrough, which is coaxial with a first longitudinal axis 22. The second section 21 has a second bore extending therethrough, which is coaxial with a second longitudinal axis 24. The first and second longitudinal axes 22, 24 are preferably angled relative to one another. As a result, the first bore extending through the first section 18 has an orientation that is non-parallel or tilted in relation to the second bore extending through the second section 21 (see FIG. 4).

Figure 4:
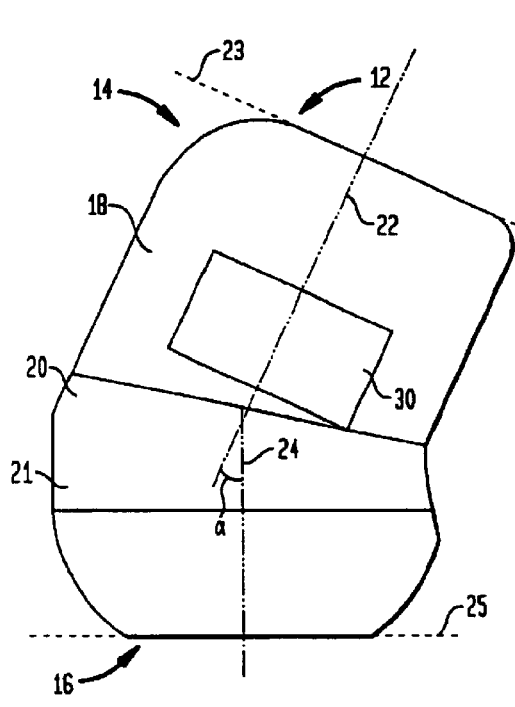
FIG. 4 is a left side elevation view of the coupling element of FIG. 3.

Referring to FIG. 4, the angle $\alpha$ formed between the first and second longitudinal axes 22, 24 may comprise any angle greater than 0° up to but not including 90°. The specific angle $\alpha$ may depend upon the particular application for the fixation assembly 10. Preferably, the angle $\alpha$ is approximately between 20–30°. In more preferred embodiments, the angle $\alpha$ is approximately 25°±2°. In highly preferred embodiments, the angle $\alpha$ is approximately 24°. The coupling elements 12 may be provided in a set, with each coupling element 12 having a slightly different shape and unique angle. During surgery, a surgeon may select a coupling element from the set having an appropriate angle for the particular patient and/or the particular location along a patient's spine.

The coupling element 12 may have other shapes, such as a Polyaxial structure having more than two cylinders (e.g., three), with each cylinder transverse to the other cylinders. In other preferred embodiments, the cylinders may have non-circular cross-sectional shapes, such as square, pentagonal, elliptical, etc.

Figure 5:
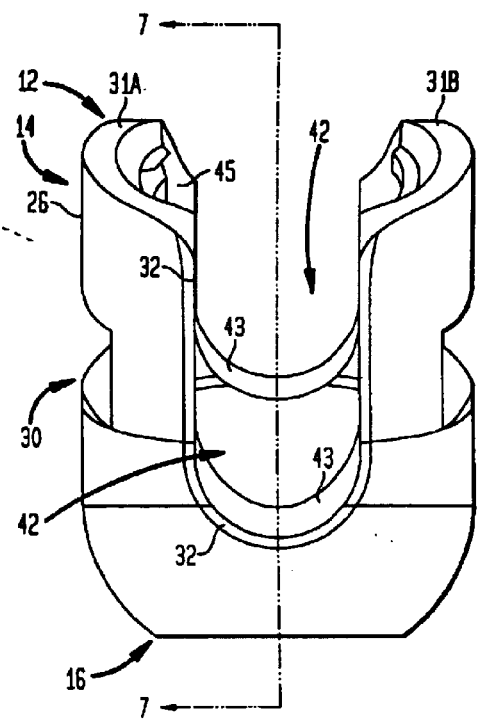
FIG. 5 is a front elevation view of the coupling element of FIGS. 3–4.
Figure 6:
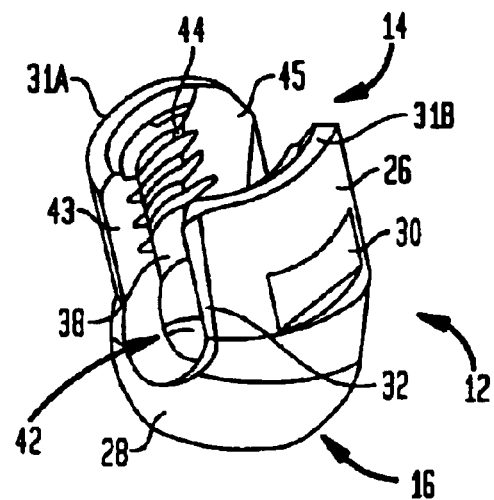
FIG. 6 is a perspective view of the coupling element of FIGS. 3–5.
Figure 7:
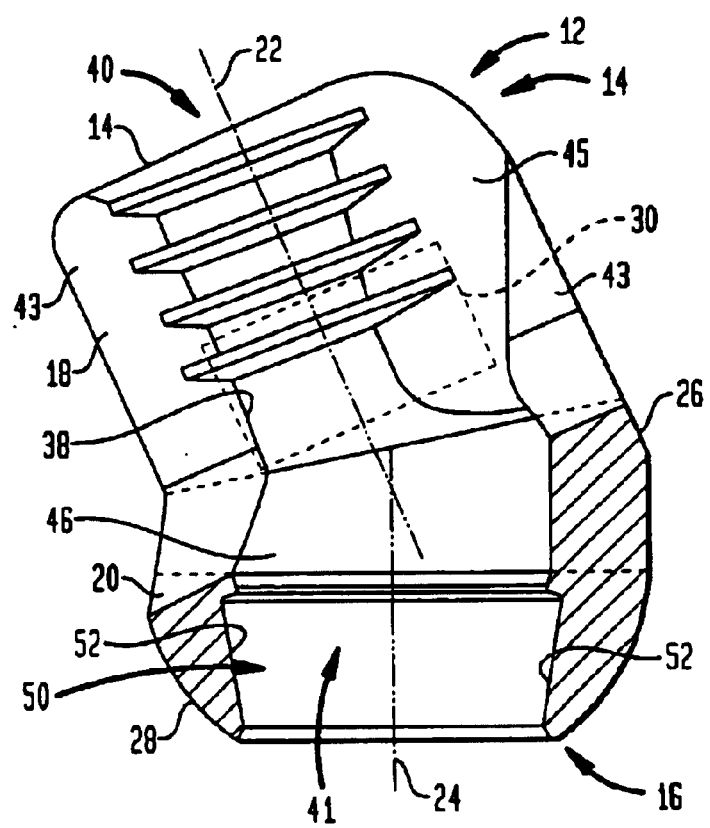
FIG. 7 is a cross-sectional view of the coupling element of FIG. 5 taken along line 7—7 thereof.

Referring to FIGS. 5–7, coupling element 12 also desirably has a substantially cylindrical outer surface 26 that extends from upper end 14 to a convex surface 28 adjacent lower end 16. Coupling element 12 also preferably includes one or more notches 30 formed in outer surface 26 so that coupling element 12 may be secured by a tool, such as a persuader instrument. The notches 30 preferably extend in directions transverse to the first longitudinal axis 22.

Referring to FIG. 7, coupling element 12 has an inner surface 38 surrounding the first bore 40, which extends from upper end 14 toward lower end 16 and is preferably coaxial with first longitudinal axis 22. The inner surface 38 preferably includes internal threads 44 extending from upper end 14 toward lower end 16. The coupling element 12 has second bore 41 that extends from lower end 16 toward upper end 14. The second bore 41 is coaxial with second longitudinal axis 24.

Referring to FIGS. 5–6, coupling element 12 has a pair of rod receiving openings 42 that extend from outer surface 26 to inner surface 38, each rod receiving opening 42 communicating with first bore 40. The rod receiving openings 42 are adapted to capture and seat an orthopedic stabilizing rod therein. The rod receiving openings 42 preferably comprise U-shaped openings having the respective open ends adjacent upper end 14 of coupling element 12 and the respective closed ends remote from the open ends.

The rod-receiving openings divide coupling element 12 into a first arm 31A on one side of the openings 42 and a second arm 31B on an opposite side of the rod-receiving openings 42. The rod-receiving openings 42 preferably include cuts 32 formed adjacent outer surface 26 of coupling element 12. Although the present invention is not limited by any particular theory of operation, it is believed that the cuts 32 enable two or more coupling elements 12 to be packed closer together than would be possible for coupling elements having the cuts omitted.

Referring to FIGS. 6 and 7, the coupling element 12 preferably has a chamfer 45 that extends from upper end 14 toward an internal cavity 46. The chamfer 45 preferably extends between the opening surface 43 of one of the rod receiving openings 42 to the inner surface 38 on the first section 18. The chamfer 45 facilitates the insertion of an anchoring element into the coupling element 12; notwithstanding the angle of first bore 40 with respect to second bore 41. In certain preferred embodiments, the chamfer 45 is bored out of the material of coupling element 12 to essentially form a third axis that is coaxial with second bore 41 and second axis 24. The chamfer 43 preferably provides room for an anchoring element and driver to pass therethrough when securing the anchoring element in bone. In other preferred embodiments, the dimensions of the coupling element and anchoring element may be selected to allow the anchoring element to be inserted into the coupling element, without requiring a chamfer.

Referring to FIG. 7, coupling element 12 includes a seat 50 adjacent lower end 16 for engaging an anchoring element. The seat 50 preferably has a conical shape with sidewalls 52 tapering inwardly toward lower end 16. In other preferred embodiments, the seat 50 is substantially spherical or concave in shape.

Referring to FIGS. 8–9, the fixation assembly preferably includes an anchoring element 52, such as a screw fastener, having a tip end 54 for insertion into bone, a head 56 at an upper end thereof, and external screw threads 58 that extend between tip end 54 and head 56. The screw threads 58 have an inner diameter 64 and an outer diameter 66. The screw threads 58 desirably terminate at a neck 60 preferably located between head 56 and screw threads 58. The neck has a neck diameter 68 that is less than the outer diameter 66 of the screw threads. The reduced diameter neck 60 allows the coupling element 12 to pivot and rotate through a broader range of motion relative to anchoring element 52. The anchoring element 52, including the screw threads 58, neck 60 and head 56, are preferably made of a biologically inert material, such as titanium or stainless steel.

Head 56 desirably includes one or more depressions or grooves 70 adapted to cooperate with a driver used to screw the anchoring element 52 into bone. Head 56 is preferably sized and shaped to pass through the first and second bores formed in coupling element 12 until an underside of head engages the seat 50 (FIG. 7) of the coupling element. The head 56 has an underside 57 that is preferably convex or spherical in shape for engaging the seat 50. When the underside 57 of head 56 engages the seat, the tip end 54 and threaded portion 58 of the anchoring element 52 extend through the second bore 41 (FIG. 7) at the lower end 16 of coupling element 12.

Figure 10:
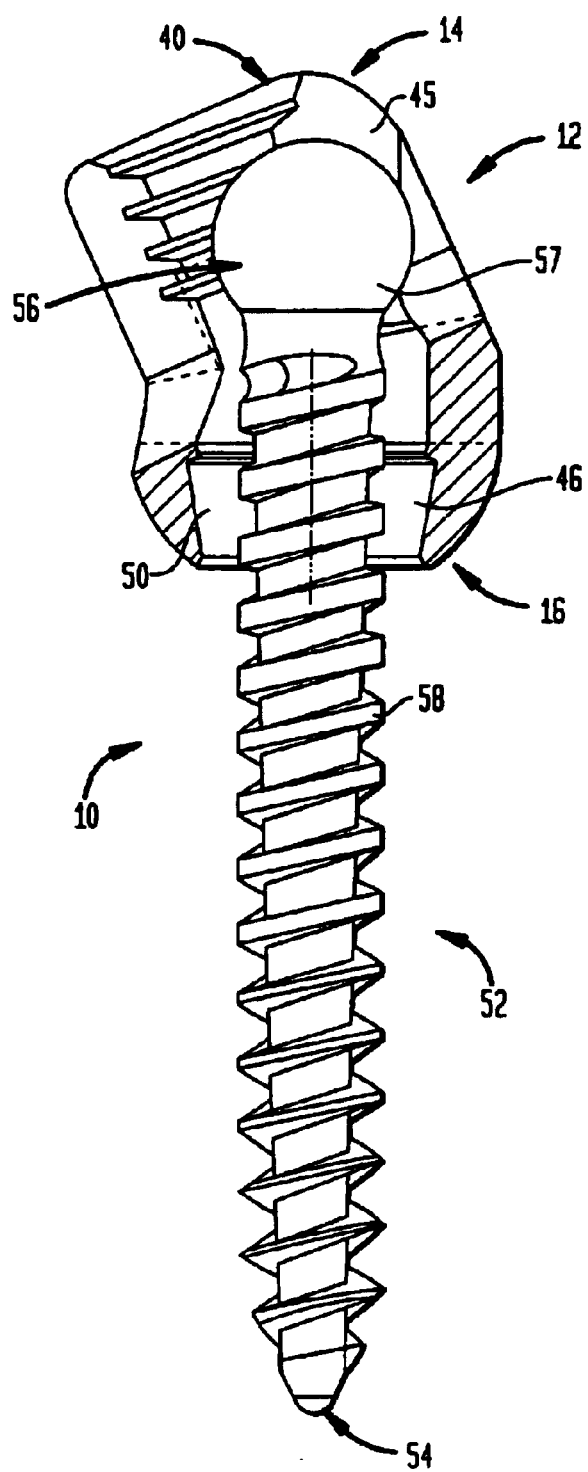
FIG. 10 is a right side elevation view, partially in section, of the anchoring element of FIGS. 8–9 partially assembled with the coupling element of FIGS. 3–7.
Figure 11:
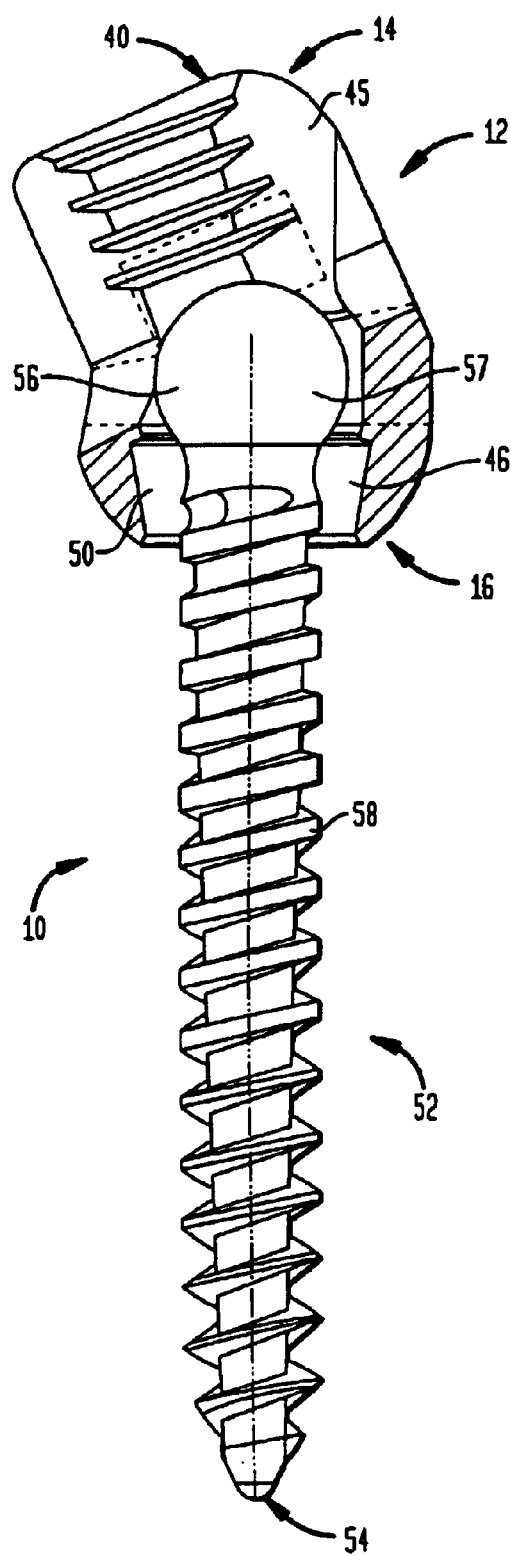
FIG. 11 is a right side elevation view, partially in section, of the coupling element and anchoring element of FIG. 10 during a further assembly step.
Figure 12:
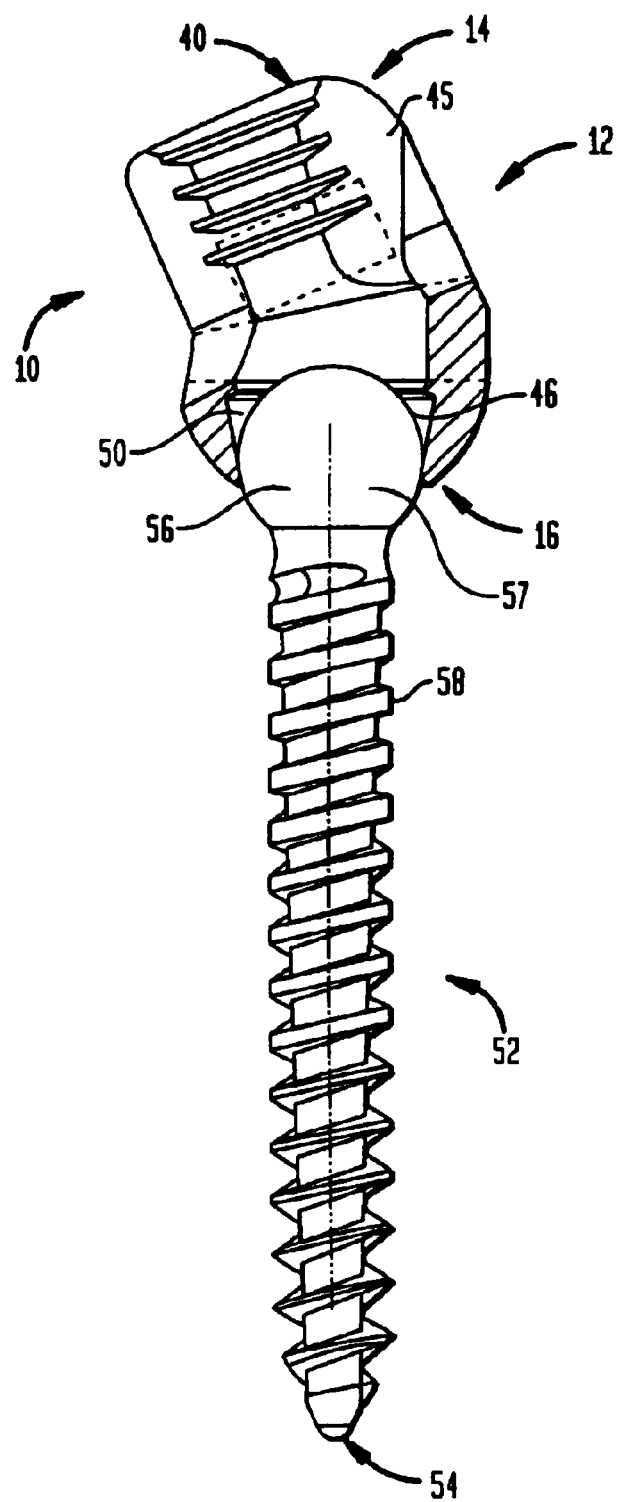
FIG. 12 is a right side elevation view, partially in section, of the coupling element and anchoring element of FIG. 11, whereby the anchoring element is fully seated in the coupling element.

Referring to FIGS. 10–12, in one preferred method for assembling anchoring element 52 with coupling element 12, the tip end 54 of anchoring element 52 is passed through first bore 40 toward lower end 16 so that screw threads 58 project from the lower end 16 of coupling element. In certain preferred embodiments, the anchoring element 52 may pass freely through first bore 40 because the outer diameter of the screw threads 58 may be less than the diameter of first bore 40. In other preferred embodiments, the diameter of the threads 58 is substantially similar to the diameter of first bore 40, requiring the anchoring element to be threaded into the coupling element until the underside 57 of head 56 engages seat 50. In certain preferred embodiments, the underside 57 of head 56 is spherical and the seat is conical-shaped. In other embodiments, the underside 57 of head 56 and seat 50 comprise other shapes, such as a convex underside and a concave seat.

Figure 13:
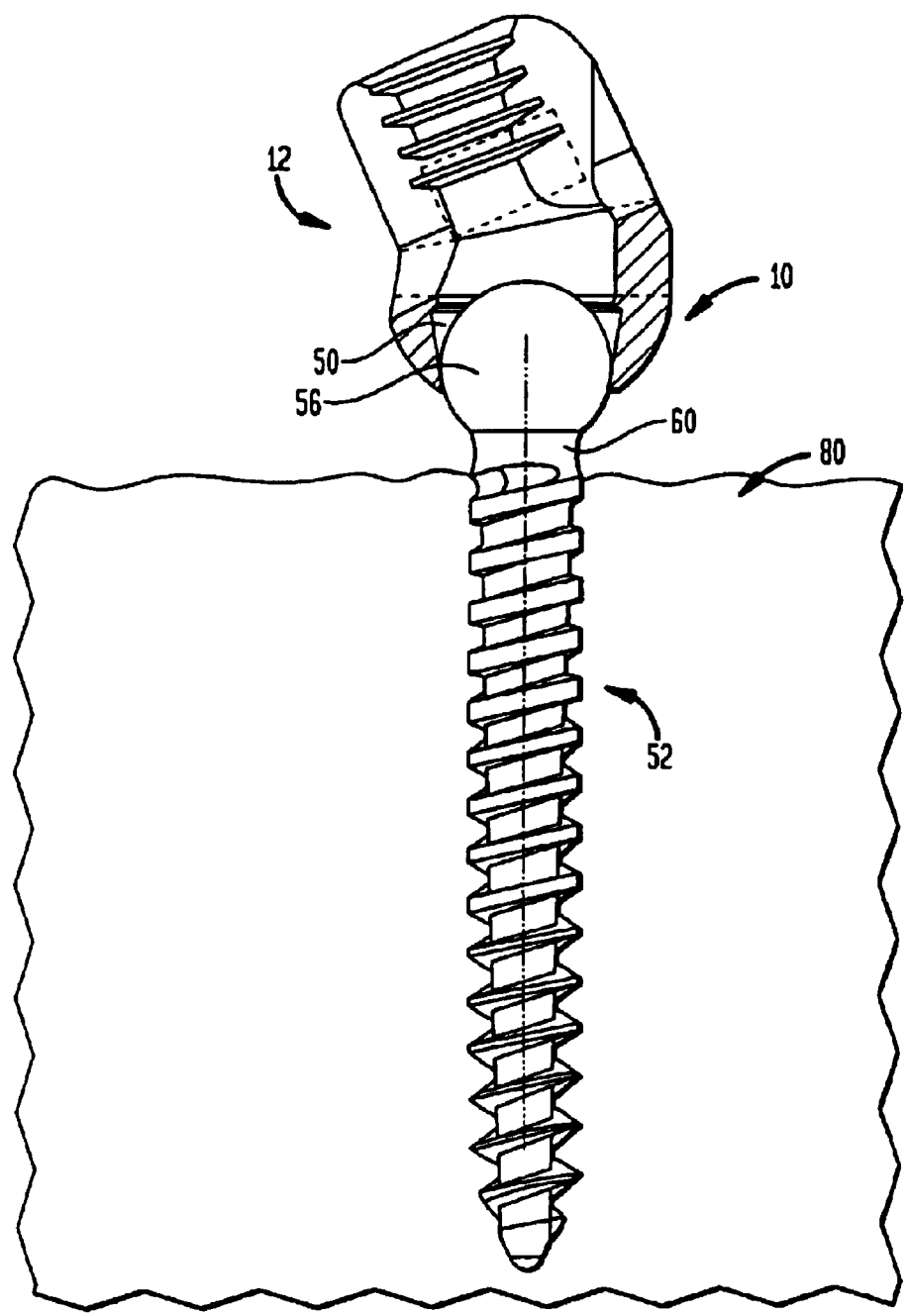
FIG. 13 is a right side elevation view, partially in section, of the coupling element and anchoring element of FIGS. 10–12, with the anchoring element secured in bone.
Figure 14:
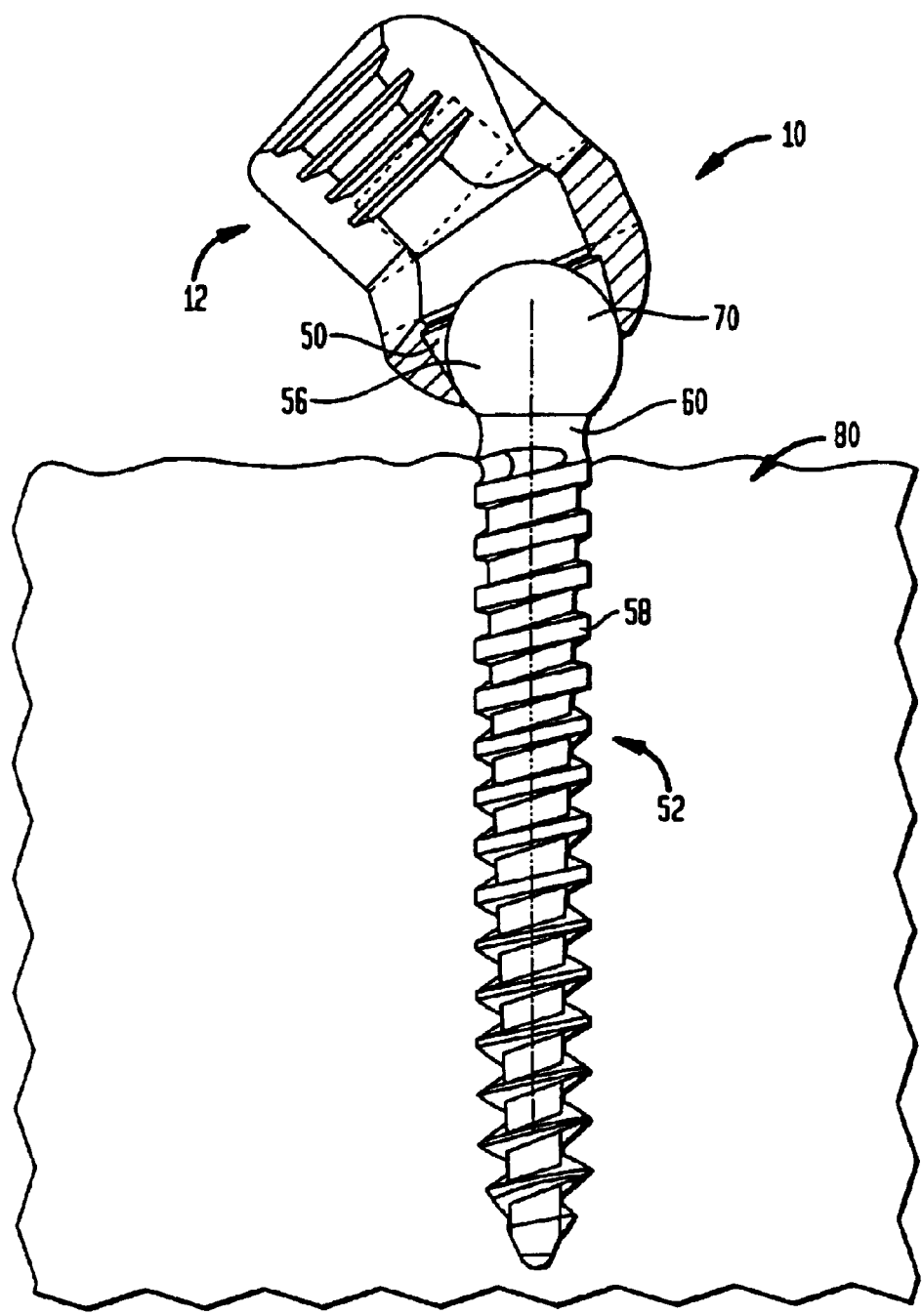
FIG. 14 is a right side elevation view, partially in section, of the coupling element and anchoring element of FIG. 13, with the coupling element pivoted about a head of the anchoring element.

Referring to FIGS. 13 and 14, after anchoring element 52 has been assembled with coupling element 12, anchoring element 52 and coupling element 12 are free to pivot and rotate relative to one another. The neck 60 of anchoring element 52 preferably has a reduced diameter with a concave outer surface 62 so that anchoring element 52 and coupling element 12 may pivot over a broader range of angles relative to one another, as compared to an anchoring element on which a reduced diameter neck is omitted. FIG. 13 shows coupling element 12 in a first position with respect to anchoring element 52. FIG. 14 shows coupling element 12 in a second position with respect to anchoring element 52 after coupling element has been rotated counterclockwise relative to the position shown in FIG. 13.

After anchoring element 52 and coupling element 12 have been assembled together, the subassembly is ready to be inserted into bone 80. In one preferred embodiment, a pilot hole is drilled in bone, and anchoring element 52 is placed in the pilot hole and screwed into the bone 80 using a driver or tool. As anchoring element 52 is rotated by driver, the anchoring element advances longitudinally into the bone 80. The anchoring element 52 is preferably advanced into the bone 80 until it is firmly secured in place such as when the neck 60 of anchoring element is adjacent the bone 80. In other preferred embodiments, the tip end includes a cutting edge formed therein such as a cutting flute, so that preforming a pilot hole is not required.

After anchoring element 52 is anchored in bone 80, coupling element 12 remains free to pivot and rotate relative to anchoring element 52 so that an orthopedic stabilizing rod 82 may be captured within the rod receiving openings 42 of coupling element 12. In certain preferred embodiments, after the anchoring element has been fully inserted into bone, a gap may exist between the lower end 16 of coupling element 12 and bone 80. The gap preferably facilitates pivotal and rotational movement of coupling element 12 relative to anchoring element 52. In other preferred embodiments, the lower end 16 of coupling element 12 may engage bone during a stabilizing procedure when the rod 82 is captured by coupling element 12. In these embodiments, however, it is not critical that the lower end 16 of the coupling element 12 contact bone in order to form a reliable assembly. In other preferred embodiments, it may be necessary for the lower end 16 of coupling element 12 to engage bone to provide a reliable, stable assembly. The coupling element 12 may be moved (e.g. pivoted) by grasping the coupling element with a tool.

Figure 15:
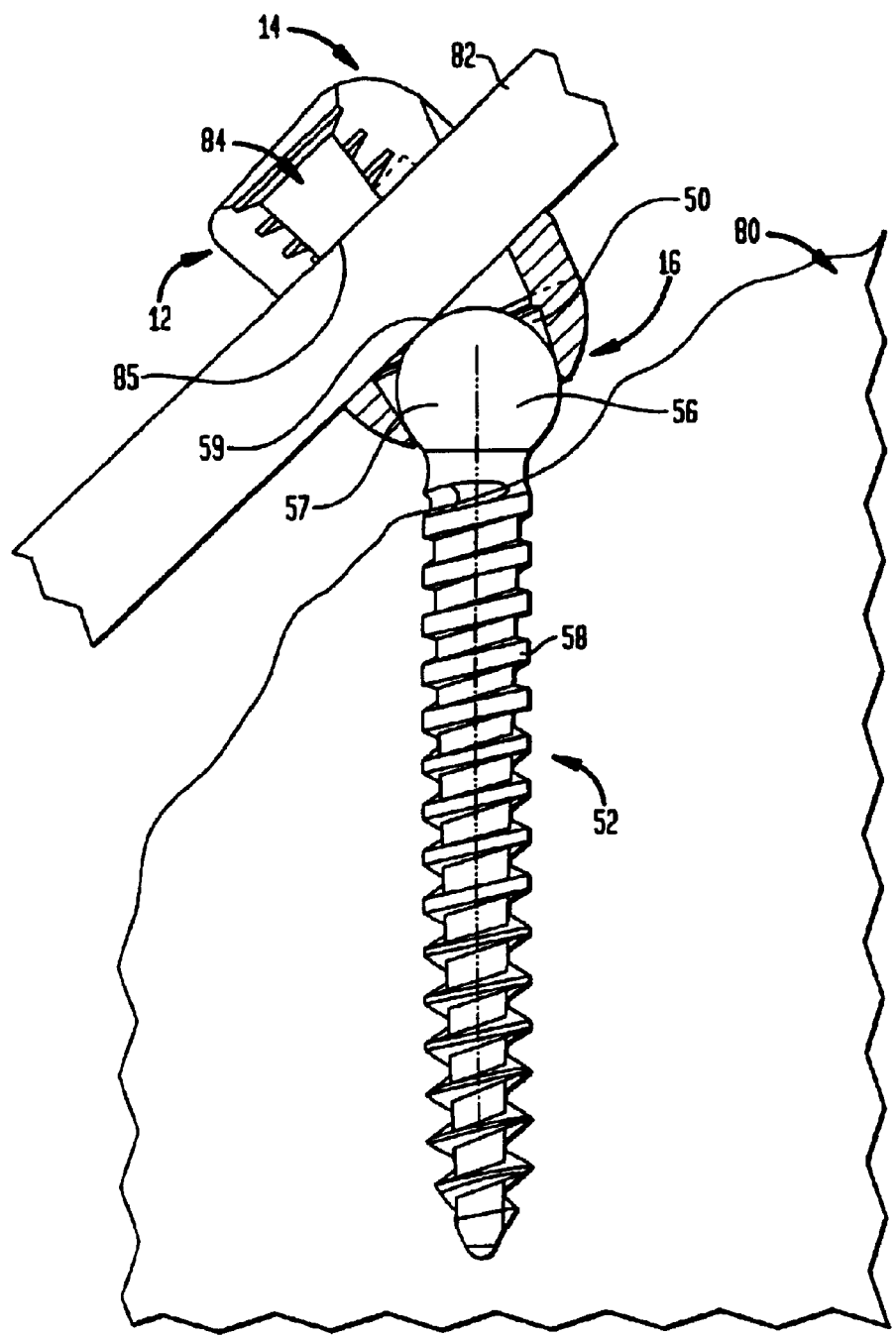
FIG. 15 is a right side elevation view, partially in section, of the bone fixation assembly of FIG. 14 with a spine rod captured in the coupling element and held in place by a locking element.

Referring to FIG. 15, after rod 82 has been positioned within coupling element 12, a locking element 84 such as a set screw having external threads, is threaded into internal threads 44 of coupling element 12 until an underside 85 of locking element 84 abuts against rod 82. Locking element 84 is then further tightened for forcing rod 82 against the closed ends of the rod receiving openings 42. The tightened locking element 84 applies a downward force through rod 82 onto the top side 59 of head 56. In other embodiments, the coupling element 12 has threads on its outer surface 26 and the locking element comprises an internally threaded sleeve.

Figure 16:
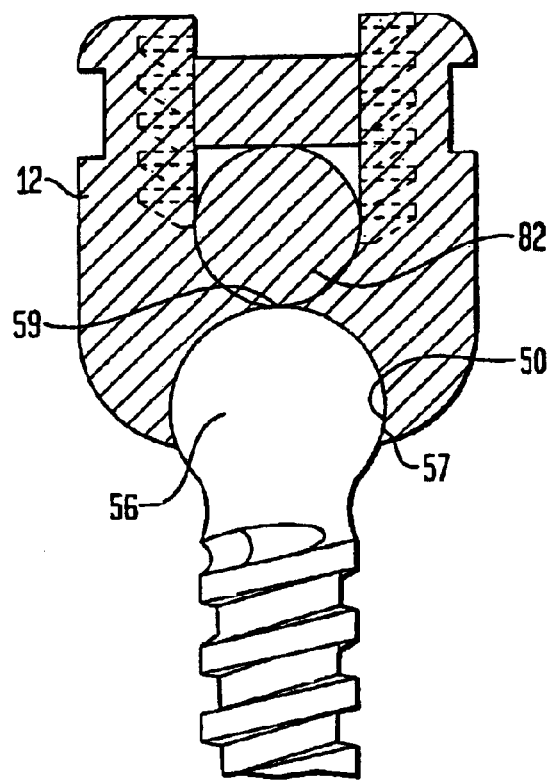
FIG. 16 is a front elevation view, partially in section, of the coupling element, anchoring element, of locking element and spinal rod shown in FIG. 16.
Figure 17:
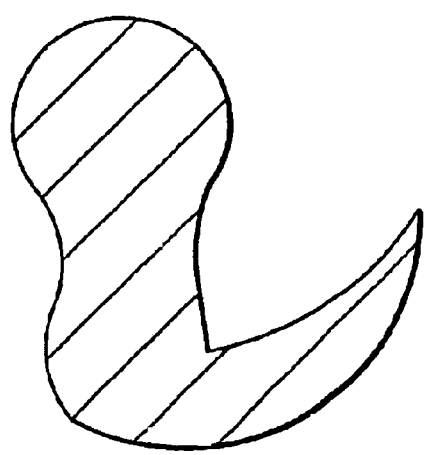
FIG. 17 is a cross-sectional view of an anchoring element of a bone fixation assembly, in accordance with another preferred embodiment of the invention.
Figure 18:
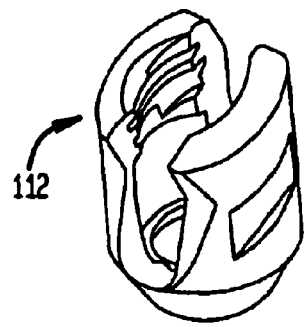
FIG. 18 is a perspective view of a coupling element of a bone fixation assembly, in accordance with another preferred embodiment of the present invention.
Figure 19:
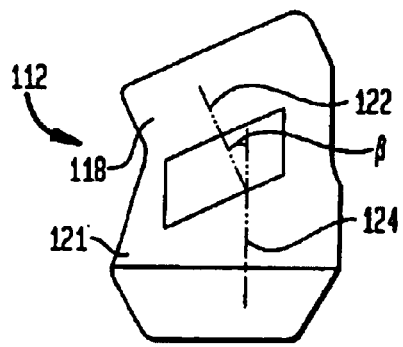
FIG. 19 is a right side elevation view of the coupling element of FIG. 18.
Figure 20:
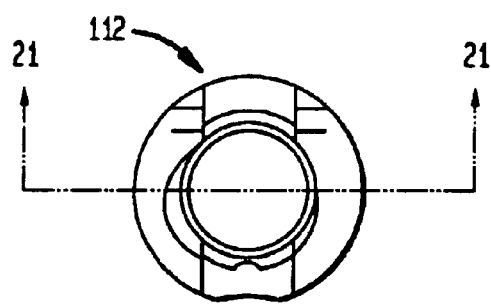
FIG. 20 is a top plan view of the coupling element of FIGS. 18–19.
Figure 21:
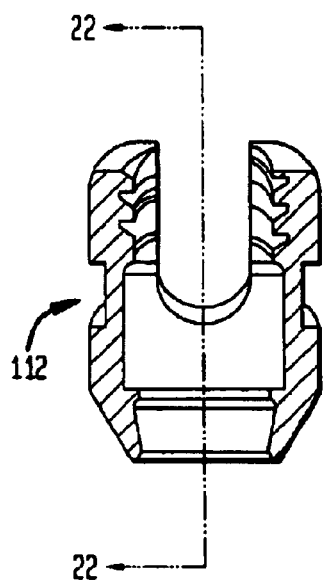
FIG. 21 is the cross-sectional view of the coupling element of FIG. 20 taken along line 21—21 in FIG. 20.
Figure 22:
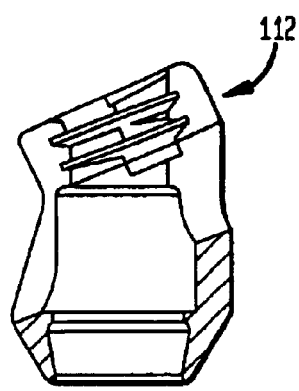
FIG. 22 is the cross-sectional view of the coupling element of FIG. 21 taken along line 22—22 in FIG. 21.

Referring to FIGS. 15–16, the downward force applied by rod 82 to the top side 59 of head 56 forces the underside 57 of head 56 into the seat 50 of coupling element 12. In embodiments in which the seat 50 has a conical shape and the underside 57 has a spherical shape, engagement of the underside 57 with the seat 50 creates a spherical/conical surface friction lock that locks the position of the coupling element 12 relative to the head 56, thereby preventing further pivotal and rotary movement of the coupling element 12 and anchoring element 52 relative to one another. Although the present invention is not limited by any particular theory of operation, it is believed that the engagement of the spherical underside of the head with the conical seat of the coupling element is a dramatic improvement over a convex/concave interface and dramatically improves the locking force exerted at the interface of the screwhead and the coupling element. In other embodiments, both seat 50 and underside 57 of head 56 have spherical shapes.

In the prior art, it has been observed that some patients have relatively small vertebrae, making it difficult to secure two or more bone fixation assemblies next to each other over adjacent vertebrae. As a result, in some patients, one or more vertebrae may not have a section of a stabilizing assembly attached thereto. This situation may adversely affect stabilization and fusion of a spine segment because the entire portion of the spine segment is not being stabilized. Although the present invention is not limited by any particular theory of operation, it is believed that providing cuts 32 adjacent the rod receiving openings 42 reduces the profile or width of the coupling element 12, thereby minimizing interference with neighboring coupling elements when a series of coupling elements are connected with a spine rod. The cuts 32 allow the coupling elements to be packed tightly together, thereby improving fusion of a spinal segment. Providing cuts 32 on coupling element 12 also minimizes the occurrence of sharp edges that may irritate a patient's tissue or cut through the surgical gloves of medical personnel.

In certain preferred embodiments, the head of the anchoring element preferably has an underside defining a first radial surface and a top side defining a second radial surface, as disclosed in certain embodiments of U.S. patent application Ser. No. 09/755,846, the disclosure of which is hereby incorporated by reference herein. The second radial surface has a radius that is smaller than the radius of the first radial surface, which is believed to provide a lower overall silhouette for the assembly.

Referring to FIGS. 18–22, in other preferred embodiments, coupling element 122 includes a first bore 140 extending through a first section 118 coaxial with a first longitudinal axis 122 and a second bore 141 extending through a second section 121 a second longitudinal axis 124, the first and second axis defining an angle coaxial with β that may comprise any angle greater than 0° up to but not including 90°. Preferably, an angle of between 20–30° is used. In more preferred embodiments, the angle β is preferably about 25°±2°. In highly preferred embodiments, the angle β is preferably 24°.

The present invention also preferably includes a driver, such as that disclosed in certain embodiments of U.S. patent application Ser. No. 09/755,846, filed Jan. 5, 2001, the disclosure of which is hereby incorporated by reference herein. The driver preferably has a rotatable shaft and one or more fingers extending from an end of the shaft for engaging the grooves in the head of the anchoring element. In preferred embodiments, the driver has one finger for each groove in the head of the anchoring element. The driver may also have external threads on a shaft that are adapted for engaging the internal threads of the coupling element when the anchoring element is anchored to bone. The engagement of the external threads of the driver and the internal threads of the coupling element generally stabilizes the assembly when the anchoring element is secured to bone. Specifically, the engagement of the threads prevents the coupling element from moving relative to the anchoring element when driving the anchoring element into bone, thereby facilitating bone anchoring.

The anchoring element may have expandable head, such as the expandable head disclosed in certain preferred embodiments of commonly assigned U.S. patent application Ser. No. 09/414,272, filed Oct. 7, 1999, the disclosure of which is hereby incorporated by reference herein. The expandable head has a recess and at least one slot extending between inner and outer surfaces of the head, which facilitates expansion of the head. The anchoring element of the '272 patent also has an insert which can be positioned at least partially in the recess, the insert having an outer surface and defining an outer dimension that is greater than the inner dimension of the recess. After a spinal rod has been positioned within a coupling element, a locking element associated with the coupling element locks the orthopedic rod in the rod-receiving opening. The locking element forces the orthopedic rod into the rod receiving opening, to in turn force the insert into the recess of the expandable head. As the insert is forced into the recess, the outer dimension of the insert bears against the inner dimension of the head, thereby expanding the outer surface of the head against a seat of the coupling element for locking the coupling element from further pivotal movement.

Figure 23:
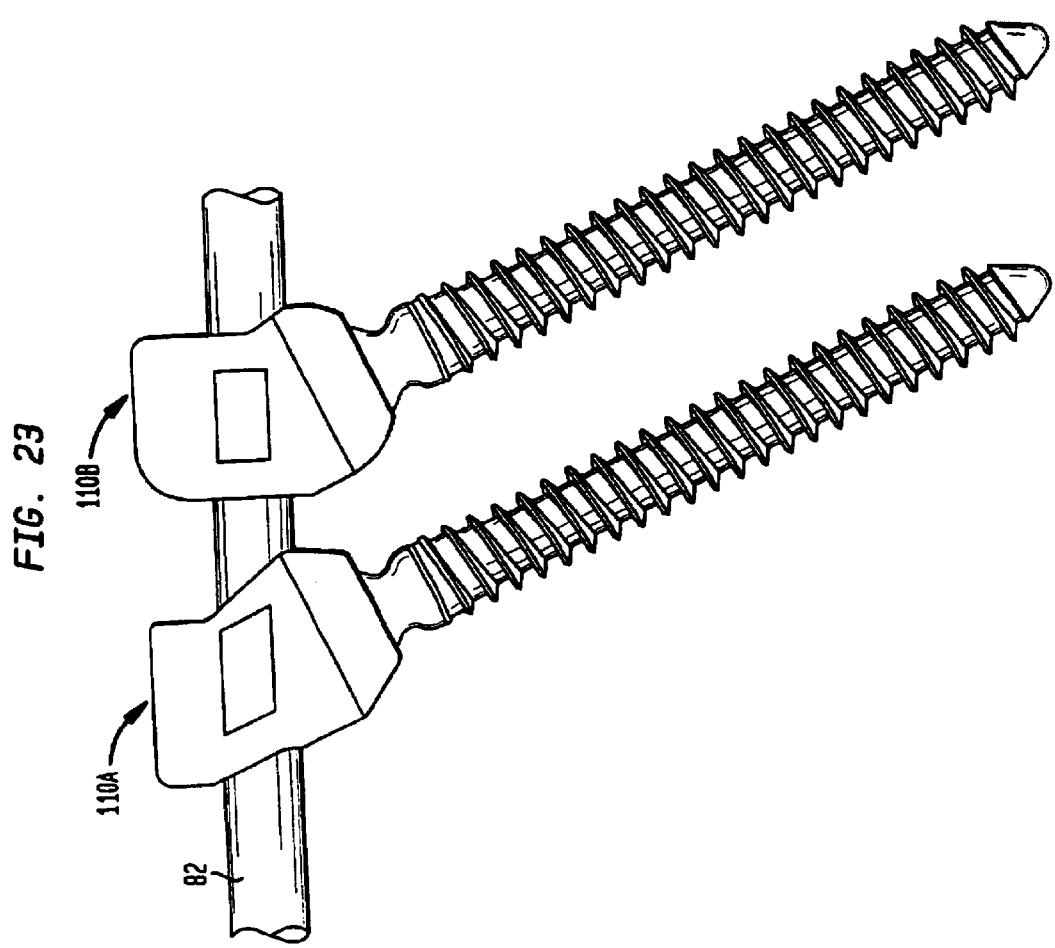
FIG. 23 is an elevation view of two bone fixation assemblies secured to a stabilizing rod, in accordance with preferred embodiments of the present invention.
Figure 24:
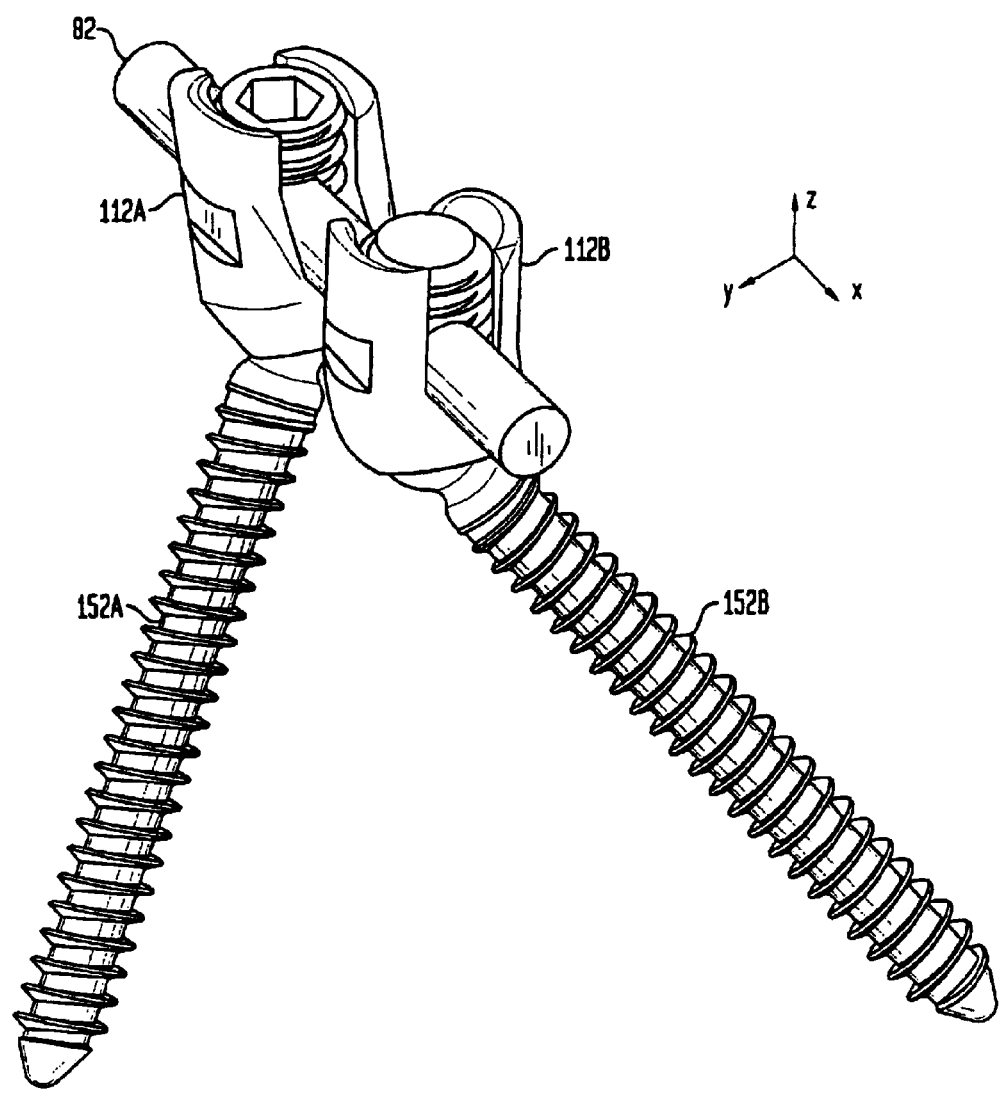
FIG. 24 is a perspective view of the two bone fixation assemblies of FIG. 23.

As shown in FIG. 23, pedicle fixation assemblies 110A, 110B may be mounted adjacent one another so as to engage a spinal rod 82. As shown in FIG. 24, the anchoring elements 152A, 152B may be locked in place with respect to the coupling elements 112A, 112B so as to form angles with respect to the spinal rod 82, in the xy, xz, or yz planes.

Figure 25:
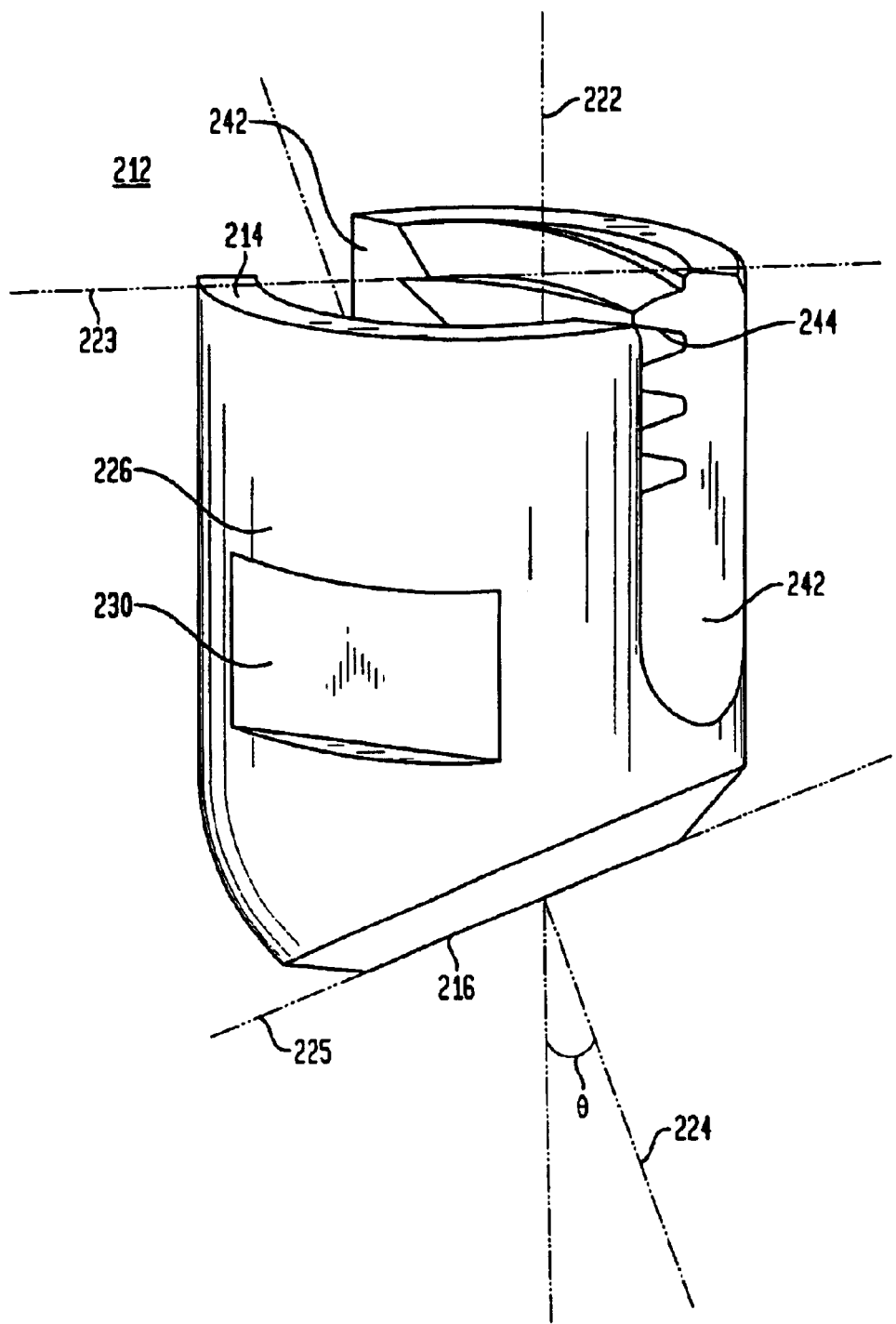
FIG. 25 is a perspective view of a coupling element of a bone fixation assembly, in accordance with further preferred embodiments of the present invention.
Figure 26:
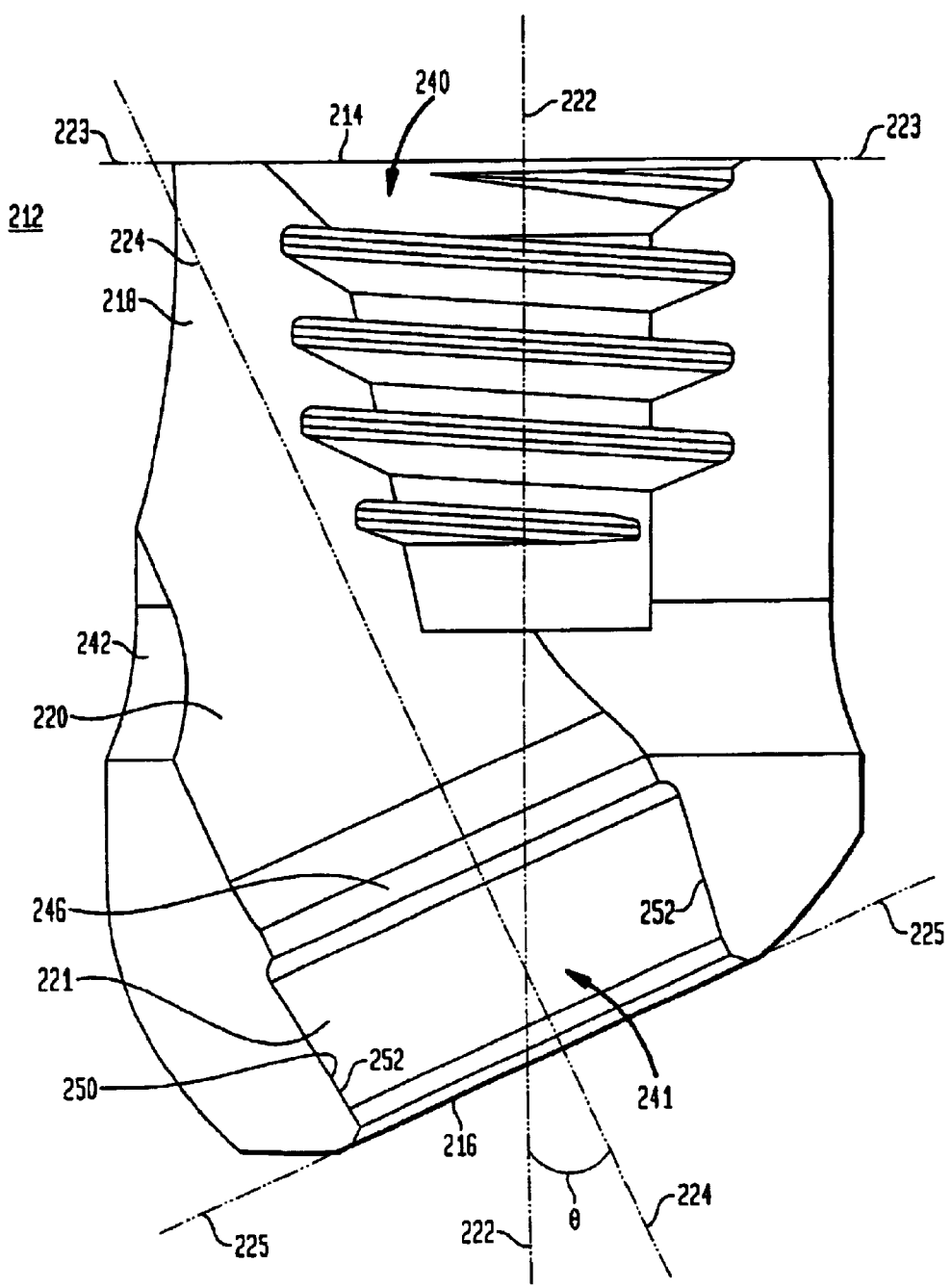
FIG. 26 is a cross sectional view of the coupling element of FIG. 25.
Figure 27:
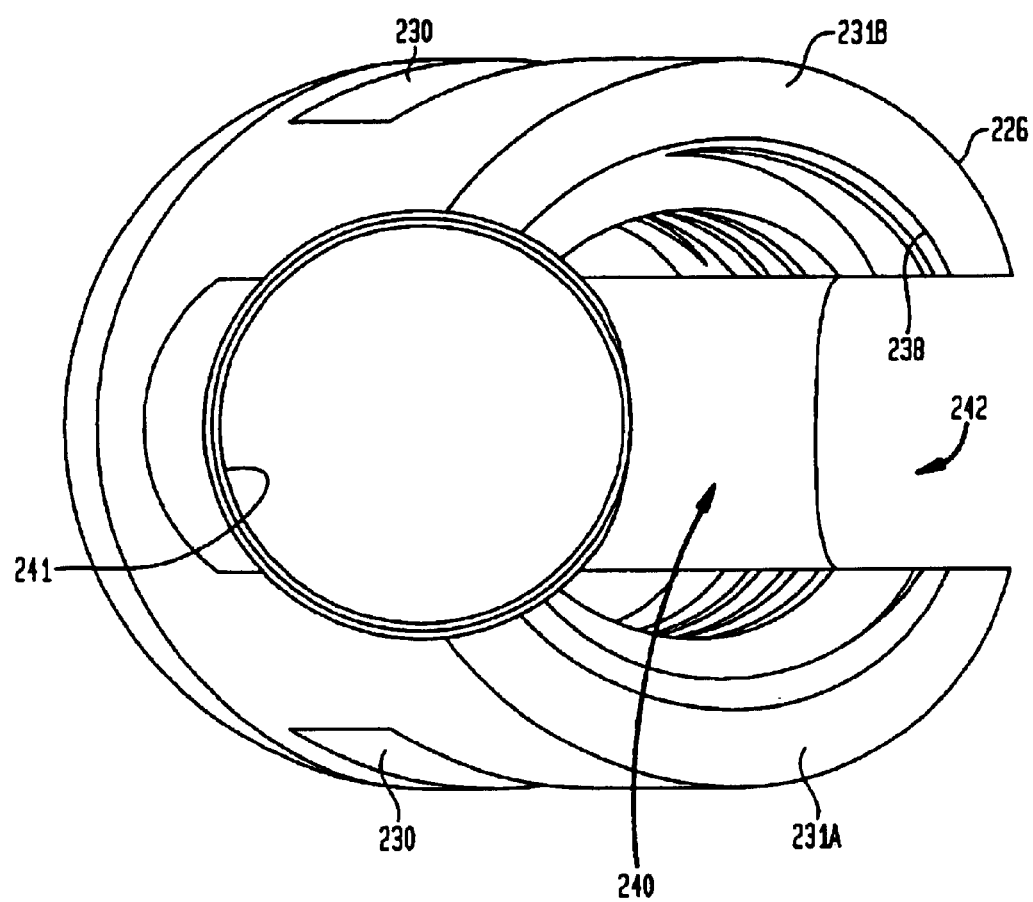
FIG. 27 is a top view of the coupling element of FIG. 26 taken along axis B—B thereof.

FIGS. 25–27 show a coupling element 212 for a pedicle fixation assembly in accordance with another preferred embodiment of the present invention. Coupling element 212 has an upper end 214 and a lower end 216, the upper end 214 defining a first plane 223 and the lower end 216 defining a second plane 225, the first and second planes 223, 225 intersecting one another.

Referring to FIGS. 26–27, coupling element 212 has a first bore 240 that extends along first axis 222 from upper end 214 to an intermediate region 220, and a second bore 241 that extends along second axis 224 from lower end 216 of coupling element 212 to intermediate region 220. The first bore 240 and second bore 241 are generally oriented non-parallel or transverse to one another.

The angle θ between first axis 222 coaxial with first bore 240 and second axis 224 coaxial with second bore 241 may comprise any angle greater than 0° up to but less than 90°. The angle θ may vary depending upon the particular application for the coupling element 212. Preferably, the angle θ is approximately between 20–30°. In more preferred embodiments, the angle θ is approximately 25°±2°. In highly preferred embodiments, the angle θ is approximately 24°.

Referring to FIG. 25, coupling element 212 desirably has an outer surface 226 that is cylindrical in shape, extending from upper end 214 to lower end 216. Outer surface 226 preferably includes one or more notches 230 formed therein so that coupling element 212 may be grasped and/or maneuvered using a securing element or tool. The notches 230 preferably extend in directions that intersect first longitudinal axis 222.

Referring to FIGS. 25–27, the first section 218 of coupling element 212 preferably includes internal threads 244 extending from upper end 214 toward lower end 216. Coupling element 212 has a pair of rod receiving openings 242 in communication with first bore 240 that extend from outer surface 226 to inner surface 238 of coupling element 212. The rod receiving openings 242 are adapted to seat a spinal rod (not shown) therein. The rod receiving openings 242 preferably comprise U-shaped openings having open ends adjacent upper end 214 and closed ends opposite the open ends. The rod-receiving openings 242 divide coupling element 212 into a first arm 231A and a second arm 231B.

The coupling element 212 has a cavity 246 in second section 221 and a seat 250 for engaging an anchoring element. In the particular preferred embodiment shown in FIG. 26, seat 250 is a conical-shaped seat including sidewalls 252 tapering inwardly toward one another adjacent lower end 216. In other preferred embodiments, seat 250 may be substantially spherical or concave.

Figure 28A:
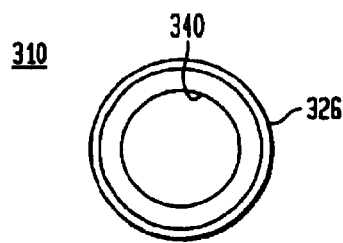
FIGS. 28A and 28B show respective top plan and side elevation views of a blank used to make a coupling element of a bone fixation assembly, in accordance with certain preferred embodiments of the present invention.
Figure 28B:
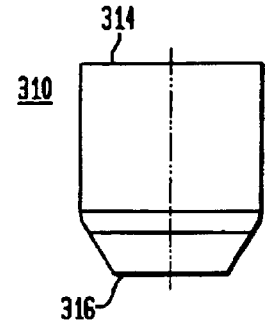

FIGS. 28A and 28B show a metal blank 310 used to make a coupling element, in accordance with other preferred embodiments of the present invention. The metal blank 310 preferably has a cylindrical outer surface 326, a longitudinal axis designated A—A, and a lower end 316 that is chamfered. The metal blank 310 is bored from upper end 314 toward lower end 316 to form first bore 340 coaxial with longitudinal axis A—A.

Figure 29:
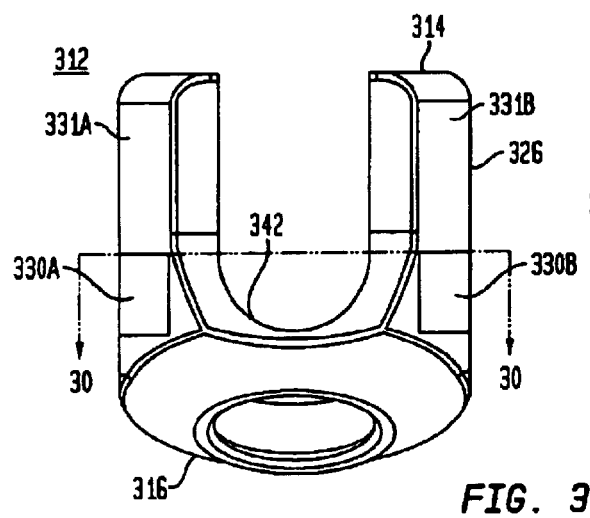
FIG. 29 shows a front elevation view of a coupling element, in accordance with certain preferred embodiments of the present invention.
Figure 30:
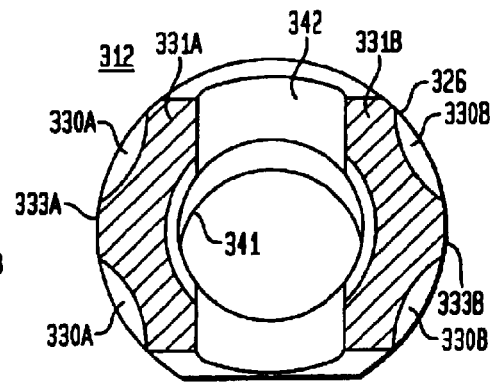
FIG. 30 shows a top plan view of the coupling element of FIG. 29 along axis A—A thereof.
Figure 31:
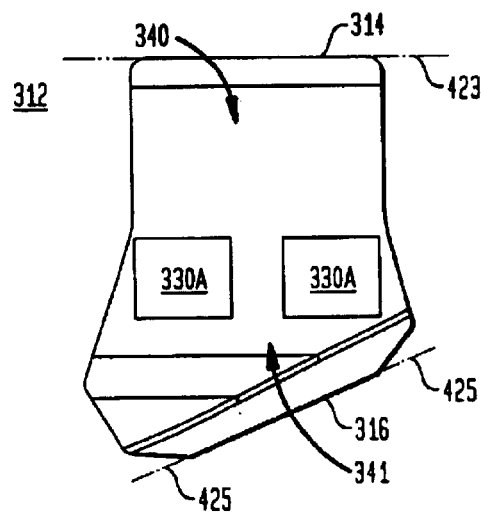
FIG. 31 shows a side elevational view of the coupling element of FIG. 29.

Referring to FIGS. 29–31, coupling element 312 has a rod-receiving opening 342 that divides opposing arms 331A, 331B from one another. The coupling element 312 has an outer surface 326 including a pair of gripping notches 30A, 30B on each opposing arm 331A, 331B. The opposing gripping notches 330A, 330B may be secured with a tool, such as forceps (not shown).

Referring to FIGS. 30–31, the opposing pairs of gripping notches 330A, 330B are cut into the respective arms 331A, 331B of coupling element 312. In certain preferred embodiments, the gripping notches 330A, 330B are formed using a rotary cutter, such as a woodruff cutter, that is abutted laterally against exterior surface 326 of coupling element 312. A first pair of gripping notches 330A on first arm 331A are separated from one another by a first rib 333A extending therebetween. Similarly, a second pair of gripping notches 330B on second arm 331B are separated from one another by second rib 333B. Coupling element 312 has two bores extending therethrough. A first bore 340 extends in a direction substantially parallel to the axis designated A—A. The first bore 340 is preferably formed by drilling from the upper end 314 toward the lower end 316 of the coupling element 312. Coupling element 312 also includes a second bore 341 extending from the lower end 316 toward upper end 314 along axis B—B. In certain preferred embodiments, the first and second bores 340, 341 may not extend completely through the length of coupling element 312, but may meet at an intermediate region between upper end 314 and lower end 316.

Referring to FIG. 31, first bore 340 is coaxial with axis A—A and second bore 341 is coaxial with axis B—B. The first bore 340 extends from upper end 314 toward lower end 316 of coupling element 312, and second bore 341 extends from lower end 316 toward upper end 314. Upper end 314 of coupling element 312 defines a first plane 423 and lower end 316 defines a second plane 425. The first and second planes 423, 425 are preferably angled relative to one another and intersect one another.

Figure 32A:
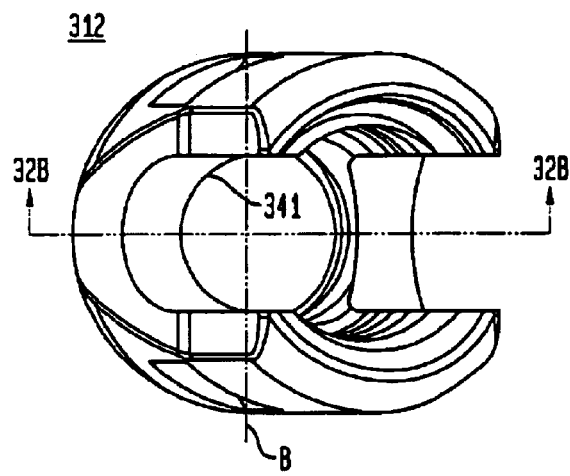
FIG. 32A shows a top plan view of the coupling element of FIG. 31 along axis B—B thereof.
Figure 32B:
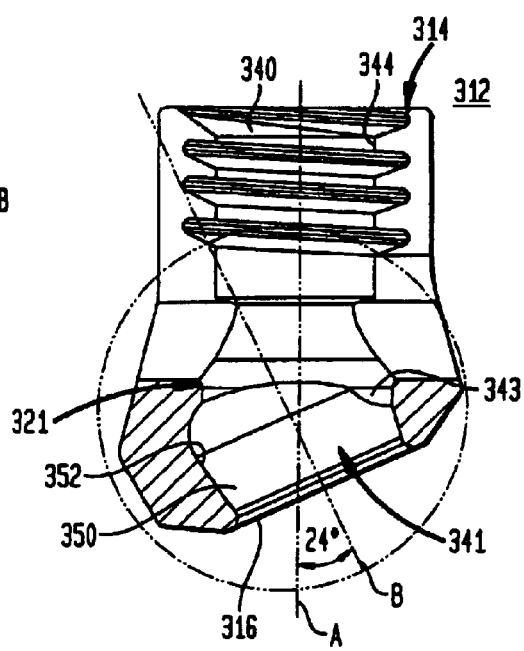
FIG. 32B shows a cross-sectional view of the coupling element of FIG. 32A taken along line 32B—32B thereof.
Figures 1, 32B:
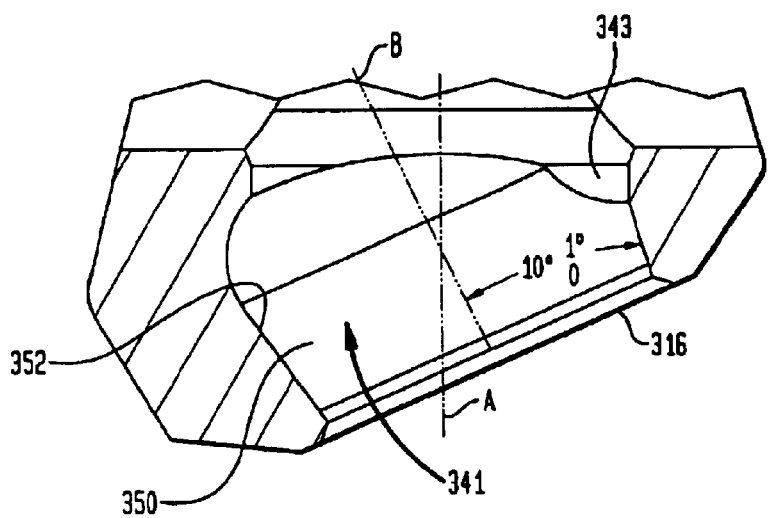

FIG. 32A shows coupling element 312 including second bore 341 formed from lower end 316 thereof and extending along axis B—B. Referring to FIG. 32B, first bore 340 is coaxial with axis A—A and second bore 341 is coaxial with axis B—B. Coupling element 312 includes internal threads 344 extending from upper end 314 toward lower end 316. The exterior surface of coupling element 312 adjacent lower end 316 is preferably chamfered. In certain preferred embodiments, the chamfered surface is formed by rotating coupling element 312 about axis B—B and engaging lower end 316 with a grinding tool. An intermediate region 321 of coupling element 312 includes a retaining lip 343. As will be described in more detail below, retaining lip 343 prevents an anchoring element such as a screw fastener from disassembling with coupling element 312 after the coupling element and the anchoring element have been assembled together. Second bore 341 formed in lower end 316 of coupling element 312 preferably includes a seat 350 having side walls 352 that taper inwardly toward one another. As shown in FIG. 32B-1, the side walls 352 and axis B—B preferably define an angle of approximately 8–12° and more preferably about 10°.

Referring to FIGS. 33–35B, the pedicle screw assembly of the present invention also includes anchoring element 352 having tip end 354 and head 356 remote therefrom. In certain preferred embodiments, head 356 has a spherical radius. Head 356 includes evenly spaced cuts 370 formed in the exterior surface of head 356. In certain preferred embodiments, the spaced cuts 370 are made using a grinding or milling tool that engages the head from lateral sides. Fastening element 352 includes external screw threads 358 having an outer diameter 366 and an inner diameter 364. Fastening element 352 also includes neck 360 provided between an upper end of screw threads 358 and head 356. The neck 360 has a concave surface 362. Fastening element 352 also includes a cutting surface 371, such as a cutting flute, formed adjacent tip end 354. As is known to those skilled in the art, providing a cutting flute 371 at a tip end 354 of fastening element 352 avoids the need to pre-tap into bone, which in turn provides for a tighter, snugger fit between the fastening element 352 and bone. As the fastening element 352 is screwed into bone, the cutting flute 371 cuts into the bone, thereby avoiding the need to pre-tap the bone. When screwing fastening element 352 in bone, the evenly spaced cuts 370 on head 356 are engaged by the fingers of a driver, as will be described in more detail below.

Figure 36A:
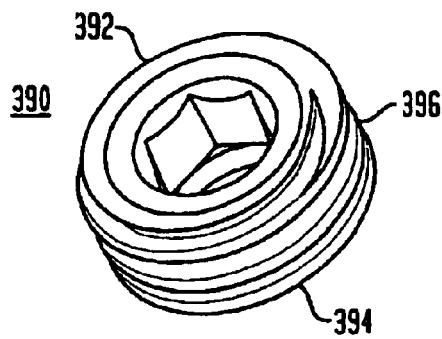
FIGS. 36A–36C show respective perspective, top plan and cross-sectional views of a locking element threadable into the coupling element of FIGS. 29–32B-1, in accordance with certain preferred embodiments of the present invention.
Figure 36B:
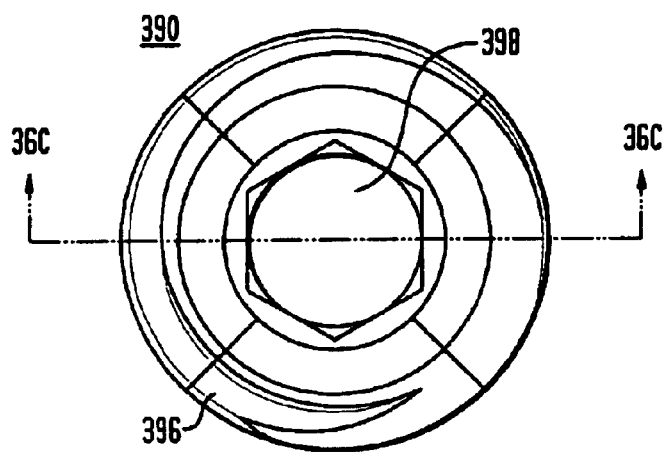
Figure 36C:
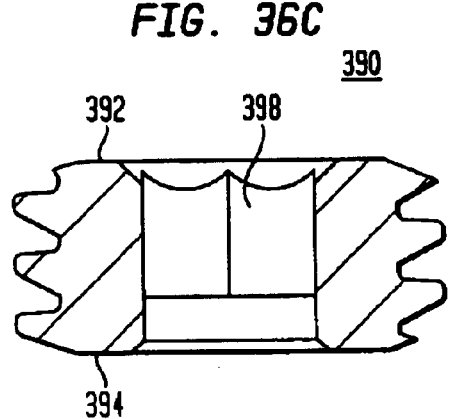
Figure 39:
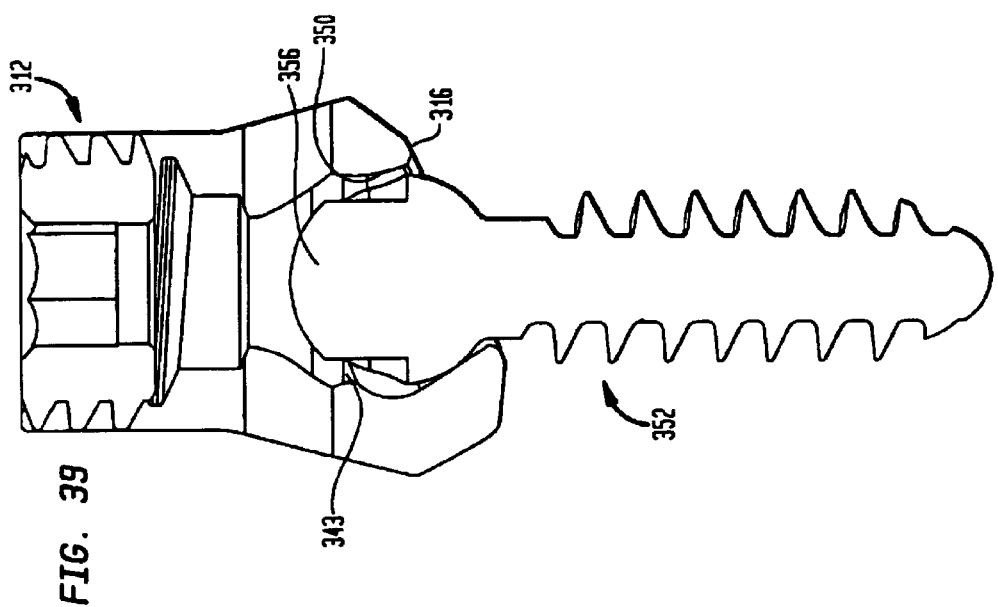
FIG. 39 shows a cross-sectional view of the bone fixation assembly shown in FIG. 37B.
Figure 37B:
FIGS. 37B and 38 show respective side elevation and front elevation views of the bone fixation assembly of FIG. 37A after the coupling element, anchoring element and locking element have been assembled together.
Figure 38:
Figure 37A:
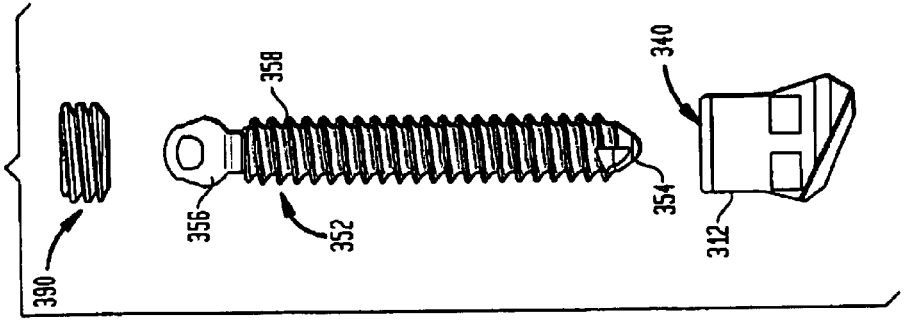
FIG. 37A shows an exploded view of a bone fixation assembly including a coupling element, a fastening element and a locking element, in accordance with certain preferred embodiments of the present invention.

Referring to FIGS. 36A–36C, fixation assembly also preferably includes a locking element such as a set screw 390 having an upper end 392, a lower end 394 and external threads 396 extending between the upper and lower ends. Set screw 390 includes a hexagonal shaped opening 398 extending from upper end 392 toward lower end 394, which is adapted to receive an end of a hexagonal driver for turning set screw 390. As will be described in more detail below, an underside 394 of set screw 390 is adapted to abut against an orthopedic stabilizing rod for exerting a downward force on a head of an anchoring element for locking fixation assembly from further movement.

FIG. 37A–39A show a fixation assembly including coupling element 312, screw fastener 352 and set screw 390 prior to the components being assembled together. In one preferred embodiment, the tip end 354 of screw fastener 352 is passed through the first bore 340 extending from upper end 314 of coupling element 312. In certain embodiments, the external threads 358 of screw fastener 352 must be threaded past internal threads (not shown) of coupling element 312, however, in other preferred embodiments, the threaded portion may pass the internal threads by rocking the threaded portion 358 back and forth until the threaded portion 358 of screw fastener 352 clears a lower end of the internal threads. After the threads 358 of screw fastener 352 have cleared the interval threads of coupling element 312, the head 356 of screw fastener 352 is press fit into seat 350 adjacent lower end 316 of coupling element 312. The head 356 of screw fastener 352 preferably has a diameter that is slightly greater than the diameter of the bore at retaining lip 343. As head 356 is pushed through retaining lip 343, the retaining lip 343 is slightly deformed to allow the head to pass into seat 350. Once head 356 passes retaining lip 343, the retaining lip 343 springs back to a diameter that is smaller than the outer diameter of head 356. As a result, head 356 is captured in seat 350 of coupling element 312 between retaining lip 343 and the opening at the lower end 316 of coupling element 312. Once the head 356 is captured within seat 350, the screw fastener 352 and coupling element 312 are able to pivot and rotate relative to one another.

Referring to FIGS. 40–42, after the head 356 of anchoring element 352 has been captured within the seat 350 of coupling element 312, the bone fixation assembly is ready to be anchored into bone and coupled with an orthopedic stabilizing rod. In one preferred embodiment, a driver 421 including shaft 423 having lower end 425 with spaced fingers 427 projecting therefrom is placed in substantial alignment over head 356 of screw fastener 352. The fingers 427 are preferably substantially rigid so as to limit flexing or bending of the fingers 427 as forces are exerted upon the fingers. The fingers 427 are then seated in spaced cuts 330 of head 356. Driver 421 also includes a shaft 423 having external threads 429 adapted to mesh with the internal threads 344 of coupling element 312 for stabilizing coupling element 312 and screw fastener 352 as screw fastener 352 is threaded into bone. Driver 421 also preferably includes a sleeve 425 slidable along shaft 423 for sliding over exterior surface 326 of coupling element 312 to further stabilize the fixation assembly when threading fastening element 352 into bone.

Although the invention herein has been described with reference to particular embodiments, it is to be understood that these embodiments are merely illustrative of the principles and applications of the present invention. It is therefore to be understood that numerous modifications may be made to the embodiments disclosed herein and that other arrangements may be devised without departing from the spirit and scope of the present invention as defined by the appended claims.

What is claimed is:

1. A bone fixation assembly comprising:
a coupling element having an inner surface defining a first bore coaxial with a first longitudinal axis and a second bore coaxial with a second longitudinal axis, wherein said first and second longitudinal axes intersect and are in communication with one another;
said coupling element including a seat adjacent said lower end of said coupling element, said seat being defined by the inner surface of said coupling element; and
an anchoring element assembled with said coupling element, said anchoring element having a first end for insertion into bone and a head spaced from the first end, said head being in contact with said seat of said coupling element.

2. The assembly of claim 1, wherein said coupling element has an upper end and a lower end, said first bore extending from said upper end toward said lower end and said second bore extending from said lower end toward said upper end.

3. The assembly of claim 2, wherein said first and second bores are in communication with one another between said upper and lower ends of said coupling element.

4. The assembly of claim 2, wherein said upper end of said coupling element defines a first plane and said lower end of said coupling element defines a second plane, and wherein said first and second planes intersect one another.

5. The assembly of claim 2, wherein said anchoring element projects from said lower end of said coupling element.

6. The assembly of claim 2, wherein said second bore includes a seat adjacent said lower end of said coupling element, and wherein said seat is adapted to engage said anchoring element.

7. The assembly of claim 6, wherein said anchoring element has a head having a substantially spherical underside adapted to engage said seat.

8. The assembly of claim 7, wherein said anchoring element includes a neck adjacent said head having a diameter less than the diameter of said threaded portion for facilitating pivotal movement of said coupling element and said anchoring element relative to one another.

9. The assembly of claim 8, wherein said neck includes a concave surface.

10. The assembly of claim 7, further comprising a locking element engageable with said coupling element for locking the position of said coupling element with respect to said anchoring element.

11. The assembly of claim 10, wherein said locking element urges a stabilizing rod toward said lower end of said coupling element which in turn forces said head of said anchoring element against said seat for locking said coupling element and said anchoring element from further movement relative to one another.

12. The assembly of claim 6, wherein said coupling element includes a chamfer adjacent said first bore for facilitating assembly of said anchoring element with said coupling element.

13. The assembly of claim 1, wherein said anchoring element is a separate member assembled with said coupling element so that said coupling element and said anchoring element are movable relative to one another.

14. The assembly of claim 1, wherein said seat is substantially conical with sidewalls tapering inwardly toward said lower end of said coupling element.

15. The assembly of claim 1, further comprising a locking element engageable with said coupling element for securing a stabilizing rod within said coupling element.

16. The assembly of claim 1, wherein said coupling element has an exterior surface, an upper end and a lower end, said rod-receiving openings extending from said upper end toward said lower end, and wherein said coupling element comprises cuts between said exterior surface and said rod-receiving openings for minimizing the width of said coupling element.

17. The assembly as claimed in claim 1, wherein said anchoring element is a screw fastener having screw threads extending from said first end toward a second end thereof.

18. A bone fixation assembly comprising:
a coupling element having an upper end defining a first plane, a lower end defining a second plane, and at least one bore extending from said upper end toward said lower end, wherein said first and second planes intersect one another;
an anchoring element assembled with said coupling element, said anchoring element being adapted for insertion into bone; and
said coupling element having a U-shaped opening that extends from the upper end of said coupling element toward the lower end of said coupling element, wherein said U-shaped opening is adapted to receive a stabilizing rod.

19. The assembly of claim 18, wherein said coupling element includes at least one bore extending between said upper end and said lower end for receiving said anchoring element.

20. The assembly of claim 18, wherein said coupling element has a seat shaped to allow said coupling element to pivot with respect to said anchoring element.

21. The assembly of claim 20, wherein said anchoring element has a head with a substantially spherical shape and said coupling element has a conical-shaped seat adjacent said lower end thereof, and wherein said spherical head is adapted to engage said conical seat.

22. The assembly of claim 21, wherein said head has at least one depression adapted to receive a driver for driving said anchoring element into bone.

23. The assembly of claim 21, wherein said anchoring element includes a reduced diameter neck for facilitating pivotal movement of said coupling element with respect to said anchoring element.

24. A coupling element having an upper end and a lower end comprising:
    a first section extending from said upper end toward said lower end of said coupling element, said first section including a first bore coaxial with a first longitudinal axis;
    a second section extending from said lower end toward said upper end of said coupling element, said second section having a second bore coaxial with a second longitudinal axis that intersects said first longitudinal axis;
    a U-shaped rod receiving opening extending from said upper end toward said lower end of said coupling element and being adapted to receive an orthopedic stabilizing rod;
    said coupling element having an inner surface defining said first and second bores and a seat adjacent said second bore at said lower end of said coupling element; and
    an anchoring element having a first end for insertion into bone and a head spaced from said first end, said head being in contact with said seat of said coupling element.

25. The coupling element of claim 24, wherein said second bore includes a seat adjacent said lower end of said coupling element.

26. The coupling element of claim 25, wherein said seat is adapted to engage a head of an anchoring element secured with said coupling element so that said coupling element and said anchoring element are pivotable relative to one another.

27. The coupling element of claim 26, wherein said seat is adapted to engage an underside of said head of said anchoring element.

28. The coupling element of claim 26, wherein said coupling element includes an inner surface defining said first and second bores, said rod receiving openings being defined by substantially U-shaped opening surfaces, and further comprising a chamfer extending from one of said opening surfaces to said inner surface.

29. The coupling element of claim 26, wherein said inner surface includes threads adjacent said upper end thereof for engaging a locking element for securing an orthopedic rod within said rod receiving openings of said coupling element.

30. The coupling element of claim 29, wherein said locking element has external threads adapted for threading into said internal threads of said coupling element.

31. The coupling element of claim 24, wherein said seat has an inwardly tapering conical shape or a convex shape.

32. The coupling element of claim 24, wherein said coupling element has an outer surface with notches for engagement by an instrument for positioning said coupling element with respect to an orthopedic rod.

33. A coupling element for a bone fixation assembly comprising:
    an upper end defining a first plane;
    a lower end defining a second plane;
    at least one bore extending between said upper end and said lower end, said at least one bore being adapted to receive an anchoring element, wherein said first plane and said second plane intersect one another;
    said coupling element having a U-shaped opening that extends from the upper end of said coupling element toward the lower end of said coupling element, wherein said U-shaped opening is adapted to receive a stabilizing rod.

34. The coupling element of claim 33, wherein said first and second intersecting planes define an angle of about 20–30°.

35. The coupling element of claim 33, wherein said first and second intersecting planes define an angle of about 25°±2°.

36. The coupling element of claim 33, wherein said first and second intersecting planes define an angle of about 24°.

37. The coupling element as claimed in claim 33, wherein said coupling element has a first bore extending from said upper end toward said lower end and a second bore extending from said lower end toward said upper end, and wherein said first and second bores are angled relative to one another.

38. A coupling element for a pedicle screw assembly, comprising:
    said coupling element including an inner surface having a first section at an upper end of said coupling element, said first section defining a first bore extending through said coupling element that is coaxial with a first longitudinal axis;
    the inner surface having a second section at a lower end of said coupling element, said second section defining a second bore extending through said coupling element that is coaxial with a second longitudinal axis, wherein said first and second longitudinal axes intersect one another.

39. The coupling element of claim 38, wherein said first and second longitudinal axes intersect one another at an angle of between about 20–30°.

* * * * *

UNITED STATES PATENT AND TRADEMARK OFFICE
CERTIFICATE OF CORRECTION

PATENT NO. : 6,974,460 B2
DATED : December 13, 2005
INVENTOR(S) : Michael Horan et al.

It is certified that error appears in the above-identified patent and that said Letters Patent is hereby corrected as shown below:

Column 1,
Line 41, delete "uses" and insert -- use --.
Line 51, delete "show" and insert -- shows --.

Column 2,
Line 60, delete "having" and insert -- has --.

Column 8,
Line 12, delete "∝" and insert -- α --.

Column 9,
Line 37, delete "are" and insert -- is --.

Column 11,
Line 42, insert -- having -- after "121".

Column 12,
Line 1, insert -- an -- after "have".

Column 14,
Line 51, delete "FIG." and insert -- FIGS. --.

Signed and Sealed this

Eighteenth Day of April, 2006

JON W. DUDAS
*Director of the United States Patent and Trademark Office*